(12) United States Patent
Nelson et al.

(10) Patent No.: US 11,766,516 B2
(45) Date of Patent: Sep. 26, 2023

(54) VACUUM ASSISTED DRAINAGE RESERVOIR AND SYSTEMS

(71) Applicant: Merit Medical Systems, Inc., South Jordan, UT (US)

(72) Inventors: Arlin D. Nelson, Sandy, UT (US); Joanne Hislop, Lehi, UT (US); Christopher Cindrich, Highland, UT (US); Andrew Hansen, Bluffdale, UT (US); Nicholas Accisano, III, Howell, NJ (US); Kenneth Sykes, Bluffdale, UT (US); Gregory R. McArthur, Sandy, UT (US); Michael Dean Haslam, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 115 days.

(21) Appl. No.: 16/781,881

(22) Filed: Feb. 4, 2020

(65) Prior Publication Data
US 2020/0246515 A1    Aug. 6, 2020

Related U.S. Application Data

(60) Provisional application No. 62/801,522, filed on Feb. 5, 2019.

(51) Int. Cl.
*A61M 1/00* (2006.01)
*A61M 39/28* (2006.01)

(52) U.S. Cl.
CPC ............. *A61M 1/964* (2021.05); *A61M 1/67* (2021.05); *A61M 1/684* (2021.05); *A61M 39/28* (2013.01);
(Continued)

(58) Field of Classification Search
CPC ........ A61M 1/68; A61M 1/684; A61M 1/682; A61M 1/80; A61M 1/82; A61M 1/0003; A61M 1/0011; A61M 5/3257; A61M 2005/3258; A61M 5/326; A61M 2005/3261; A61M 2205/071;
(Continued)

(56) References Cited

U.S. PATENT DOCUMENTS 3,421,504 A * 1/1969 Gibbons .............. A61M 1/0011
604/73
3,938,514 A * 2/1976 Boucher .............. A61M 1/0011
604/28
(Continued)

FOREIGN PATENT DOCUMENTS

KR     20170040661     4/1996
KR       200386026     5/2005
WO  WO-2019156973 A1 *  8/2019 ............... F21S 4/10

OTHER PUBLICATIONS

International Search Report dated Jun. 9, 2020 for PCT/US2020/016644.

*Primary Examiner* — Erich G Herbermann
*Assistant Examiner* — Seth Han
(74) *Attorney, Agent, or Firm* — Dorsey & Whitney LLP

(57) ABSTRACT

Devices used to drain fluid are disclosed. The devices may be configured to drain fluid from a body cavity using a vacuum pressure. The devices include a reservoir and a vacuum generating member configured to expand the reservoir and generate a vacuum pressure within the reservoir. The devices can be configured to be shipped in a collapsed state.

18 Claims, 18 Drawing Sheets

(52) U.S. Cl.
CPC . *A61M 2209/084* (2013.01); *A61M 2210/101* (2013.01)

(58) Field of Classification Search
CPC .......... A61M 2205/07; A61M 16/0075; A61M 16/0084; A61F 5/44; F04B 53/10; F04B 53/1002; F04B 53/1005; F04B 45/02; F04F 3/00
USPC ........................................................ 604/319
See application file for complete search history.

(56) References Cited

U.S. PATENT DOCUMENTS

| | | | |
|---|---|---|---|
| 4,643,719 A * | 2/1987 | Garth | A61M 1/84 604/73 |
| 5,295,963 A * | 3/1994 | Deeks | A61M 5/3257 604/110 |
| 5,313,938 A * | 5/1994 | Garfield | A61M 16/0075 128/205.16 |
| 5,505,717 A | 4/1996 | Moore | |
| 5,628,305 A * | 5/1997 | Melker | A61M 16/0075 128/205.15 |
| 5,957,897 A * | 9/1999 | Jeffrey | A61M 5/3234 604/110 |
| 8,961,448 B2 * | 2/2015 | Forsell | A61M 60/871 604/9 |
| 2006/0155237 A1 | 7/2006 | Vijay | |
| 2010/0130957 A1 | 5/2010 | Smisson, III et al. | |
| 2011/0238022 A1 * | 9/2011 | Massi | A61M 1/0011 604/319 |
| 2017/0175728 A1 * | 6/2017 | Roman | F04B 53/1005 |

* cited by examiner

VACUUM ASSISTED DRAINAGE RESERVOIR AND SYSTEMS

RELATED APPLICATIONS

This application claims priority to U.S. Provisional Application No. 62/801,522, filed on Feb. 5, 2019 and titled "Vacuum Assisted Drainage Reservoir and Systems," which is incorporated herein by reference in its entirety.

TECHNICAL FIELD

The present disclosure relates generally to devices used to drain a cavity of fluid. More specifically, the present disclosure relates to a drainage reservoir and system used to drain fluid from a cavity of a human body.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
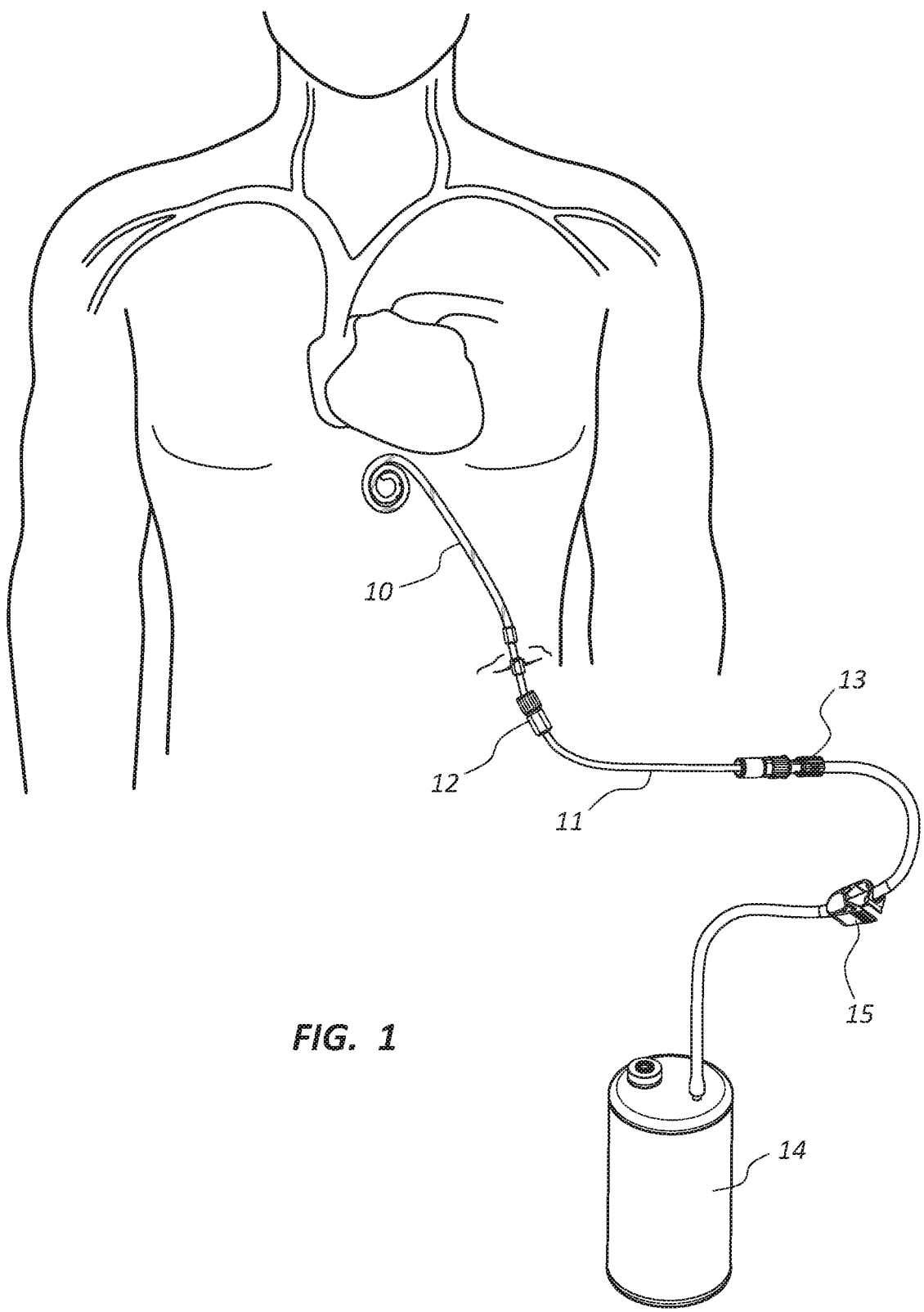
FIG. 1 is a graphic illustration of a patient and a vacuum assisted drainage system.

Fluid accumulation due to sickness or trauma may develop in areas within a mammalian body not designed to accommodate such accumulation. One particular area prone to abnormal accumulation is between sheets of tissue covering the outside of the lung and lining the chest cavity, known as the pleural space. While a normal functioning pleural space contains approximately 5-20 mL of fluid, fluid turnover occurs on an hourly basis such that approximately 5-10 L of fluid passes through the pleural space every day. Thus, any disruption in fluid turnover may result in an abnormal or over-accumulation of fluid in the pleural space, known as pleural effusion. The symptoms of pleural effusion include dyspnea, tachycardia, cough, breathing difficulty, and chest pain as the lungs are prevented from fully expanding upon breathing. Pleural effusion can also be a condition secondary to trauma, cancer, nephrotic syndrome, kidney disease, pancreatitis, congestive heart failure, and cirrhosis, and as such, patients affected with pleural effusion may die within several months of onset. Consequently, treatment of pleural effusion can be generally provided for patient quality of life in his/her final days.

There are numerous methods to treat pleural effusion and/or other unwanted fluid accumulation in a mammalian body. Fluid drainage procedures, such as thoracentesis, may be used to provide patient relief. Thoracentesis often involves the introduction of a needled catheter into the pleural space through an incision in the chest cavity, after which fluid is drawn out using a syringe or a vacuum source. Drawbacks with this procedure, however, can include the fact that the needle may inadvertently puncture a lung, leading to aggravation of the problem, and the fact that fluid readily re-accumulates in the pleural space after the procedure is performed such that it may become necessary for a patient to undergo the procedure every few days. Pleurodesis is a procedure in which fluid is prevented from accumulating due to the sealing of the space between pleura with either sterile talc or an antibiotic, after first draining the existing fluid. Another method to treat pleural effusion is to surgically implant a chest tube or catheter such that fluid accumulation can constantly or periodically be removed without invasive surgery. The implanted catheter may be connected to a drainage system that includes one or more of the following components: an external drainage tube, a one-way valve mechanism, and a collection reservoir.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the reservoir of the drainage system, the proximal end of the drainage system refers to the end nearest the bottom of the reservoir and the distal end refers to the opposite end, the end nearest the inlet port of the reservoir. Thus, if at one or more points in a procedure a physician changes the orientation of a reservoir, as used herein, the term "proximal end" always refers to the end away from the inlet port.

The phrase "vacuum pressure" refers to a gauge pressure of less than ambient atmospheric pressure. Thus, when referencing a "vacuum pressure" within a reservoir of a drainage system, the gauge pressure within the reservoir is negative or less than ambient atmospheric pressure.

"Fluid" is used in its broadest sense, to refer to any fluid, including both liquids and gases as well as fluids produced by a human body, solutions, compounds, suspensions, etc., which generally behave as fluids.

FIG. 1 illustrates an exemplary embodiment of a drainage system comprising an implanted drainage catheter 10, an external drainage tube 11, a connector 12 configured to couple the drainage catheter 10 and the external drainage tube 11, a one-way valve mechanism 13, a tube clamp 15, and a drainage reservoir 14. In some embodiments, the one-way valve mechanism 13 can be integrated into the connector 12. The drainage system permits fluid drainage through the use of gravity siphoning or a negative pressure source, such as a vacuum, or a combination of gravity siphoning and a vacuum within the collection reservoir. In certain instances, the drainage system may be configured such that the vacuum generated within the reservoir is adequate to pull or draw the fluid from the cavity without gravity siphoning (e.g., a higher pressure in the cavity can force the fluid to the reservoir which comprises a lower pressure or a vacuum). In other instances, the vacuum generated in the reservoir is used to initiate gravity siphoning.

FIGS. 2-19B illustrate different views of several drainage systems and related components. In certain views each system may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Figure 2A:
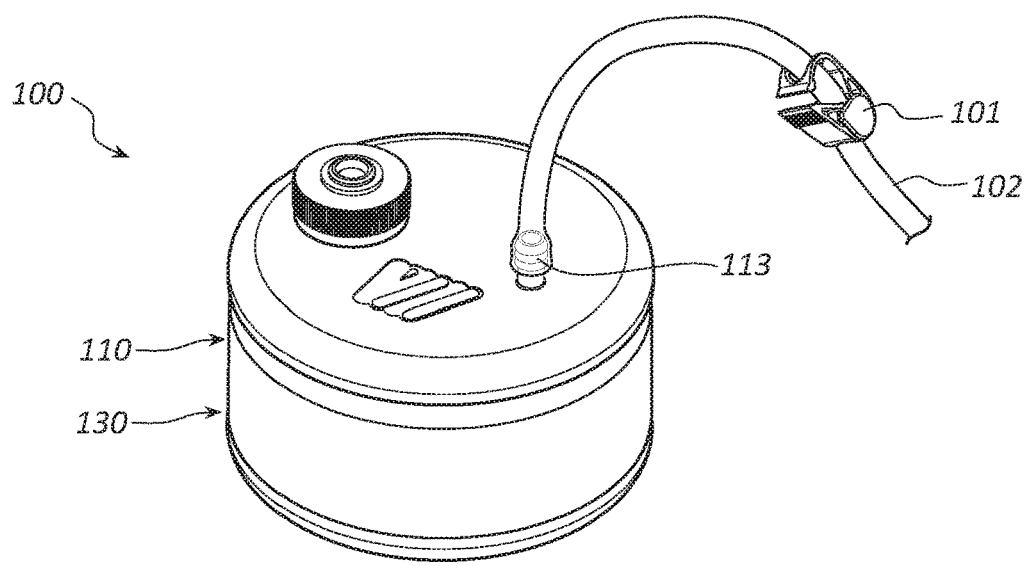
FIG. 2A is a perspective view of a vacuum assisted drainage system in a collapsed state.
Figure 2B:
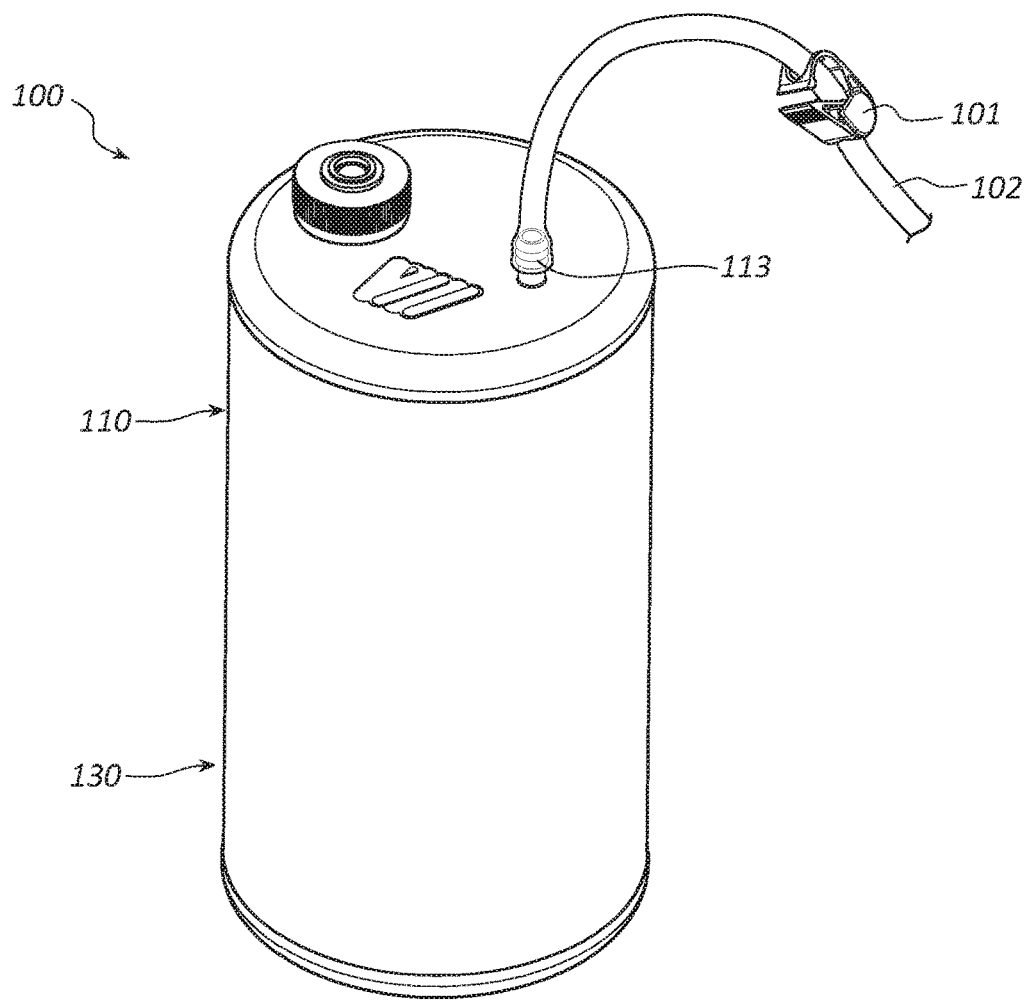
FIG. 2B is a perspective view of a vacuum assisted drainage system in an expanded state.

FIGS. 2A-2B depict an embodiment of a drainage system 100. As depicted, the drainage system includes a reservoir 110 and a vacuum generating member 130. FIG. 2A illustrates the drainage system 100 in a collapsed state where the reservoir 110 and the vacuum generating member 130 are longitudinally collapsed. FIG. 2B shows the drainage system 100 in an expanded state where the reservoir 110 and the vacuum generating member 130 are longitudinally expanded. As shown in FIGS. 2A-2B, a drainage tube 102 is coupled to and in fluid communication with the reservoir 110. A tubing clamp 101 is coupled to the drainage tube 102. In FIG. 2B, the tubing clamp 101 is shown in an open state such that drainage fluid can flow into the reservoir 110.

Figure 3A:
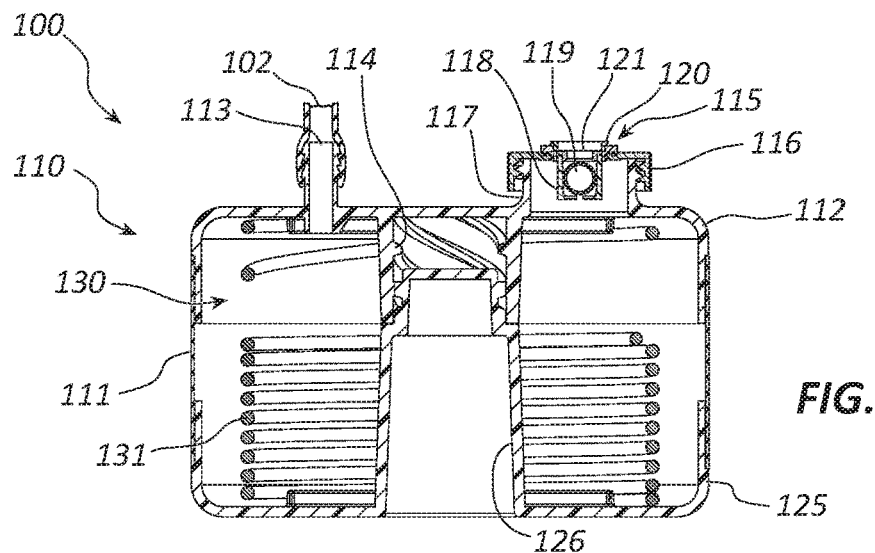
FIG. 3A is a cross-sectional view of the vacuum assisted drainage system of FIG. 2A.
Figure 3B:
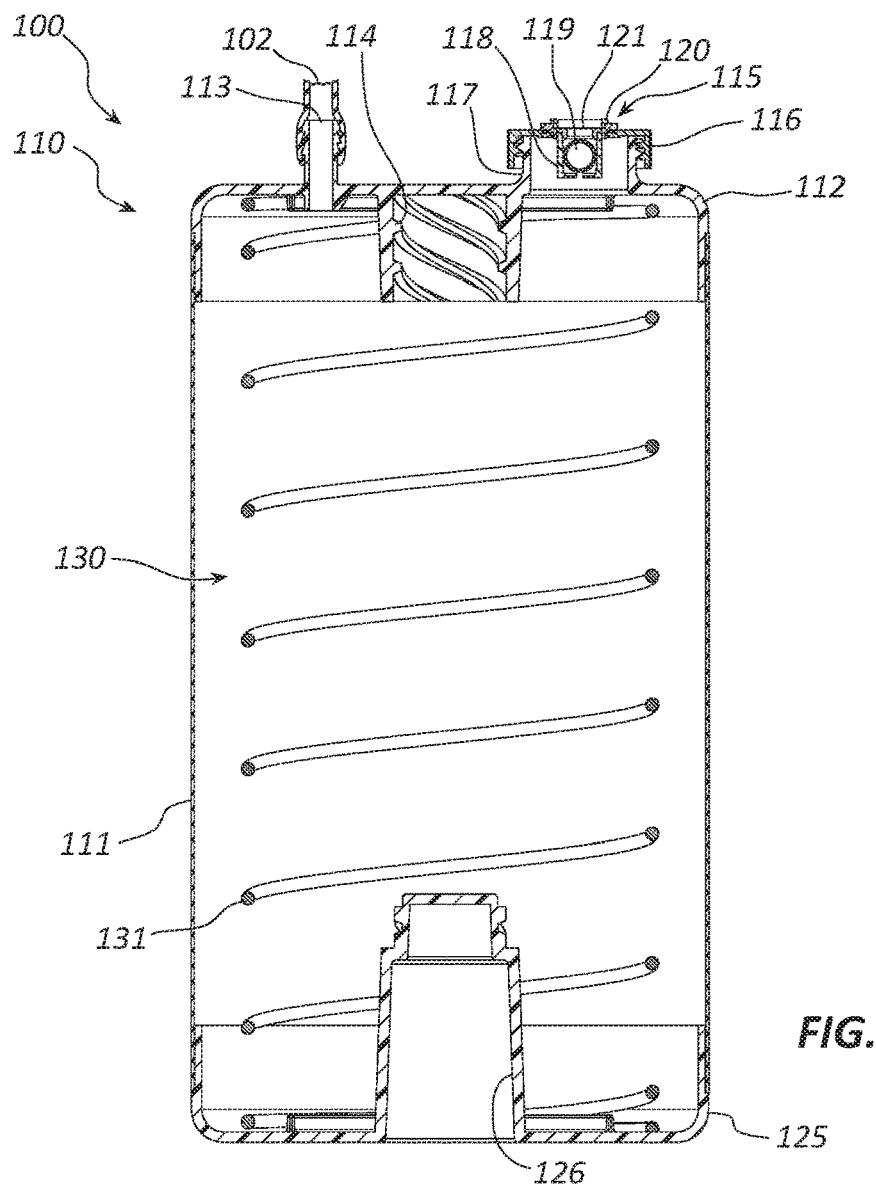
FIG. 3B is a cross-sectional view of the vacuum assisted drainage system of FIG. 2B.

FIG. 3A is a longitudinal cross-sectional view of the drainage system 100 with the reservoir 110 and a vacuum generating member 130 in the collapsed state. FIG. 3B is a longitudinal cross-sectional view of the drainage system 100 with the reservoir 110 and the vacuum generating member 130 in the expanded state. The reservoir 110 is illustrated to include a housing 111, a distal end cap 112, and a proximal end cap 125. The housing 111 may have a cylindrical shape. In other embodiments, the housing 111 may be of any suitable shape including a cone shaped with the larger diameter of the cone shape disposed adjacent the proximal end cap 125. The housing 111 is configured to retain drainage fluid and is impervious to passage of fluids and air through the wall of the housing 111. The housing 111 is configured to expand from the collapsed state as shown in FIG. 3A to the expanded state as shown in FIG. 3B. In the expanded state, the housing 111 may have an internal volume of from about 250 milliliters to about 1500 milliliters, from about 500 milliliters to about 1250 milliliters, or about 1000 milliliters. The housing 111 may be formed from any suitable flexible material or fabric that allows the housing 111 to move from the collapsed state to the expanded state and is impervious to fluid and/or air. The housing 111 may be formed from various polymeric materials. For example, the housing can comprise silicone, polyvinyl chloride, polyurethane, polyethylene, polypropylene, etc. In some embodiments, the housing 111 comprises a material that is flexible, but substantially non-elastomeric or substantially non-stretchable.

The distal end cap 112 is coupled to a distal end of the housing 111. The distal end cap 112 may be coupled to the housing 111 using any suitable manufacturing technique, such as gluing, welding, over molding, etc. In some embodiments, the distal end cap 112 may be formed from a thermoplastic material, such as polypropylene, polyethylene, polycarbonate, etc. In certain embodiments, the distal end cap 112 is formed by an injection molding technique.

As depicted, the distal end cap 112 includes an inlet port 113 extending distally from an upper surface of the distal end cap 112. The inlet port 113 includes a bore that is in fluid communication with the housing 111 and the drainage tube 102. An external portion of the inlet port 113 may be configured to frictionally and sealingly couple to the drainage tube 102. For example, the inlet port 113 may include barbs or ribs to engage with the drainage tube 102. In other embodiments, the inlet port 113 may include a seal that is penetrable by a spike (or penetrating member) coupled to a proximal end of the drainage tube 102. An internally threaded receiver 114 may extend proximally from a lower surface of the distal end cap 112. The distal end cap 112 may also include a vent port 117 extending distally from the upper surface. The vent port 117 can be configured to couple to a vent valve 115. The vent port 117 includes a bore that is in fluid communication with the housing 111. The vent port 117 may also include external threads that are configured to threadingly couple with internal threads of a vent cap 116 (or vice versa).

As illustrated in FIGS. 3A-3B, the proximal end cap 125 has a post 126 extending distally from an internal surface. The post 126 includes external threads disposed at a distal end. The external threads are configured to threadingly couple to the internal threads of the receiver 114 to maintain the reservoir 110 in the collapsed state prior to use. When in use, the post 126 can threadingly decouple from the receiver 114 to allow the drainage system 100 to expand to the expanded state. The post 126 is also configured to occupy dead space within the housing 111 when the reservoir 110 is in the collapsed state. This reduces the volume of air and increases the vacuum level within the reservoir 110 in the expanded state. In other embodiments, the distal end cap 125 comprises a post 126, and the distal end cap 112 comprises a receiver 114.

Figure 5A:
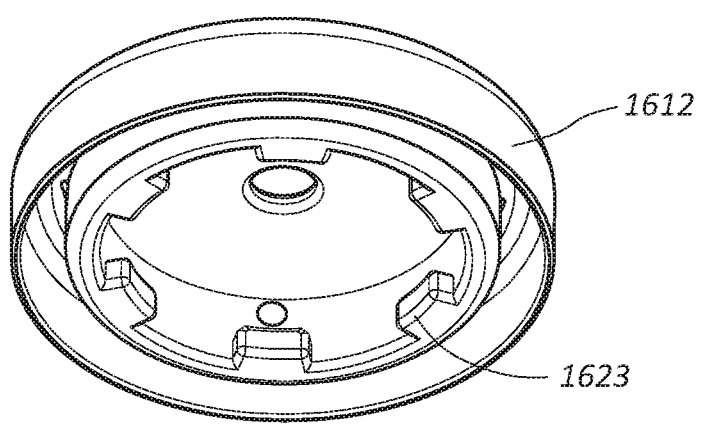
FIG. 5A is a bottom perspective view of another type of distal end cap of a vacuum assisted drainage system.
Figure 5B:
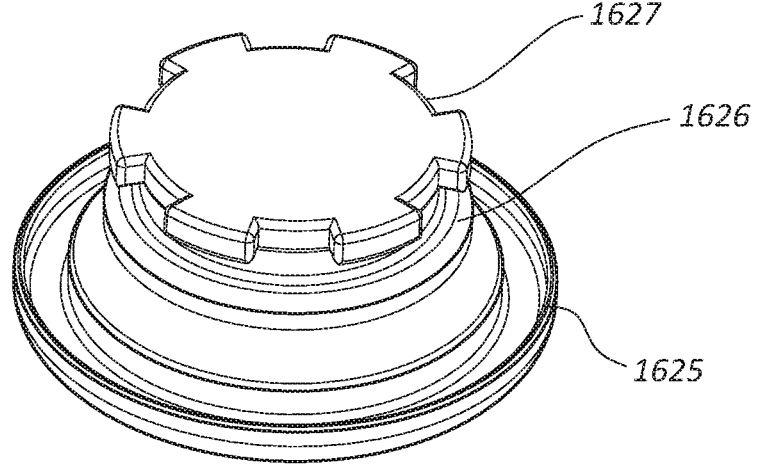
FIG. 5B is a top perspective view of another type of proximal end cap of a vacuum assisted drainage system.

FIG. 5A shows an alternative embodiment of a distal end cap 1612 and FIG. 5B shows an alternative embodiment of a proximal end cap 1625. The distal end cap 1612 is shown to have a plurality of radially inward directed lugs 1623 and the proximal end cap 1625 is shown to have a plurality of gaps 1627 configured to receive the lugs 1623. The number of gaps 1627 may match the number of lugs 1623. The number of gaps 1627 or lugs 1623 may be two, three, four, five, six, or more. When a drainage system is in the collapsed state, the lugs 1623 are disposed between and distal to the gaps 1627 to maintain the drainage system in the collapsed state prior to use. When ready for use, the distal end cap 1612 may be rotated relative to the proximal end cap 1625 such that the lugs 1623 align with the gaps 1627, allowing the lugs 1623 to pass through the gaps 1627, allowing the drainage system to expand to the expanded state. In other embodiments, the proximal end cap 1625 comprises lugs 1623, and the distal end cap 1612 comprises gaps 1627 (vice versa of FIGS. 5A and 5B). Other coupling mechanisms can also be employed. For example, the coupling mechanism may be a latch, clasp, fastener, etc.

With continued reference to FIGS. 3A-3B, the vacuum generating member 130 includes a compression spring 131 configured to expand the reservoir 110 from a collapsed state to an expanded state and to generate a vacuum pressure within the drainage system 100. The compression spring 131 may include a plurality of coils configured to be disposed within the reservoir 110. In other embodiments, the spring 131 may be disposed externally to the reservoir 110. The spring 131 may be configured to apply a longitudinal force to the reservoir 110 such that the spring 131 forces the reservoir 110 to expand from the collapsed state to the expanded state. For instance, the spring 131 can force the reservoir 110 to expand when the proximal end cap 125 is decoupled from the distal end cap 112.

Figure 4:
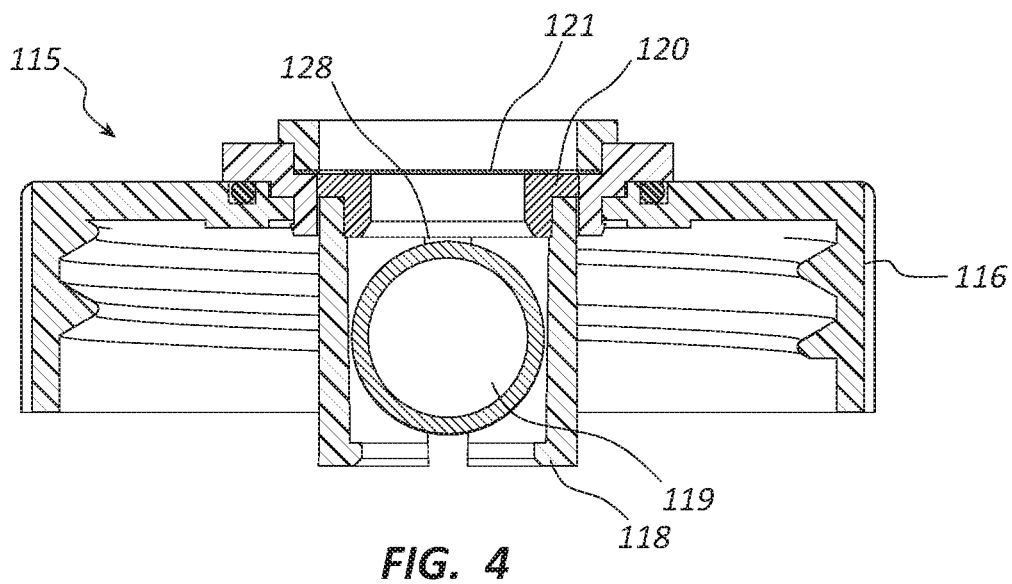
FIG. 4 is an enlarged cross-sectional view of a vent valve of FIG. 3A.

FIG. 4 illustrates the vent valve 115. As shown, the vent valve 115 comprises the internally threaded vent cap 116, a ball valve 119, and a flap valve 121. The vent cap 116 is configured to threadingly couple with the external threads of the vent port 117 (the vice versa is also contemplated). The ball valve 119 is retained within a cage 118 and the flap valve 121 is configured to rest on a valve seat 120 in a closed state. The vent valve 115 may be configured to facilitate venting of excess gas and/or air from the reservoir 110 while preventing expulsion of drainage fluid. The venting of excess gas and/or air may facilitate an increase in a vacuum pressure and drainage volume capacity. Venting of gas and/or air through the vent valve 115 may be achieved by longitudinally compressing the reservoir 110. When the reservoir 110 is compressed, the excess gas and/or air may flow into the cage 118, around the ball valve 119, through a ball valve seal 128, and displace the flap valve 121 upward such that the excess gas and/or air flows into the atmosphere. If drainage fluid is contained within the reservoir 110 when the excess gas and/or air is expelled, the drainage fluid may force the ball valve 119 upward to seal the ball valve seal 128 and prevent drainage fluid from exiting the reservoir 110. Following venting of the excess gas and/or air, compression pressure on the reservoir 110 may be released, allowing the flap valve 121 to return to a closed state where the flap valve 121 is sealingly disposed on the valve seat 120. The flap valve 121 may be maintained in the closed state by a pressure differential from outside the reservoir 110 to inside the reservoir 110. In other words, the atmospheric pressure on the outside of the reservoir 110 is greater than the vacuum pressure on the inside of the reservoir 110 and applies an inwardly directed force to the flap valve 121.

In use, the drainage system 100 may be provided to a user in the collapsed state to decrease shipping volume as illustrated in FIG. 3A. The system 100 may also optionally be packaged or configured to comprise a vacuum when in the collapsed state. For instance, the reservoir 110 can be placed in the collapsed state and air and/or fluid can be evacuated from the reservoir 110. When ready to use, the drainage tube 102 may be coupled to the inlet port 113 (e.g., via a frictional fit or via a penetrating member). In other embodiments, the drainage tube 102 may be coupled to the inlet port 113 during manufacturing. The tubing clamp 101 may optionally be in the closed state. The distal end cap 112 and the proximal end cap 125 may be decoupled (e.g. rotated relative to one another) to activate the vacuum generating member 130 and allow the spring 131 to force the reservoir 110 into the expanded state as shown in FIG. 3B. In other embodiments, a clip or band may be removed from the drainage system 100 to release the vacuum generating member 130. As the reservoir 110 expands, a vacuum pressure may be generated within the drainage system 100. The tubing clamp 101 may be opened to initiate flow (e.g., a higher pressure at a drainage site can cause the drainage fluid to flow from the patient to the vacuum pressured reservoir 110). In another embodiment, the reservoir 110 can be transitioned to the expanded state to generate a vacuum, after which a penetrating member at the end of the drainage tube 102 can be forced or pierced through a seal in the inlet port 113 to initiate drainage or flow. And in yet another embodiment, a tubing clamp 101 is not used, and flow can be initiated as the vacuum generating member 130 is activated. Excess gas and/or air within the reservoir 110 may also be expelled through the vent valve 115 at any stage by applying a compressive force to the reservoir 110.

Figure 6:
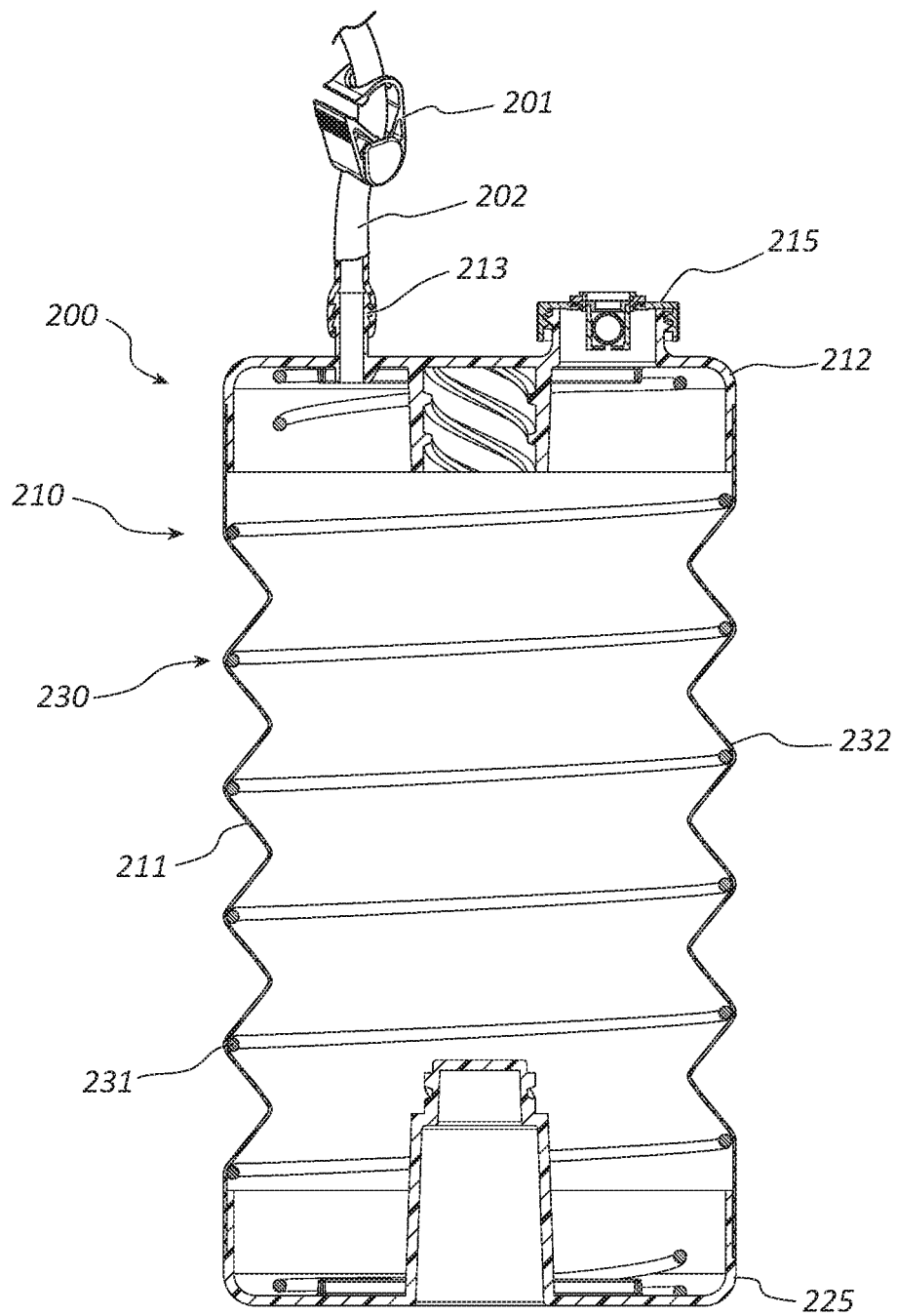
FIG. 6 is a cross-sectional view of a vacuum assisted drainage system with a concertinaed walled housing.

FIG. 6 depicts an embodiment of a drainage system 200 that resembles the drainage system 100 described above in certain respects. Accordingly, like features are designated with like reference numerals, with the leading digit incremented to "2." For example, the embodiment depicted in FIG. 6 includes a reservoir 210 that may, in some respects, resemble the reservoir 110 of FIGS. 2A-3B. Relevant disclosure set forth above regarding similarly identified features thus may not be repeated hereafter. Moreover, specific features of the drainage system 100 and related components shown in FIGS. 2A-5B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the drainage system 200 and related components depicted in FIG. 6. Any suitable combination of the features, and variations of the same, described with respect to the drainage system 100 and related components illustrated in FIGS. 2A-5B can be employed with the drainage system 200 and related components of FIG. 6, and vice versa. This pattern of disclosure applies equally to further embodiments depicted in subsequent figures and described hereafter, wherein the leading digits may be further incremented.

FIG. 6 depicts another embodiment of a drainage system 200. FIG. 6 is a longitudinal cross-sectional view of the drainage system 200 in an expanded state. As depicted, the drainage system 200 includes a reservoir 210 and a vacuum generating member 230. The reservoir 210 has a housing 211 that includes a concertinaed wall configured to expand and collapse. In other words, the housing 211 includes a wall having a series of folds 232 configured to collapse upon one another when the drainage system 200 is in a collapsed state and to separate from one another when the drainage system 200 is in an expanded state. The reservoir 210 may be formed of any suitable flexible material or fabric that is impervious to water and air, such as polymeric materials, silicone, polyvinyl chloride, polyurethane, polyethylene, polypropylene, etc. In some embodiments, the housing 111 comprises a material that is flexible, but substantially non-elastomeric or substantially non-stretchable. As shown, the reservoir 210 also includes a proximal end cap 225 and a distal end cap 212. The distal end cap 212 includes an inlet port 213 and a vent valve 215. A drainage tube 202 is coupled to the inlet port 213 and a tubing clamp 201 is coupled to the drainage tube 202. A drainage tube 202 having a penetrating member or tip can also be used with an inlet port 213 having a seal.

As illustrated in FIG. 6, the vacuum generating member 230 includes a compression spring 231 configured to longitudinally expand the reservoir 210 from a collapsed state to an expanded state and to generate a vacuum pressure within the drainage system 200. The compression spring 231 may include a plurality of coils configured to be disposed within the folds 232 of the reservoir 210. FIG. 6 depicts the spring 231 disposed within the reservoir 210. In other embodiments, the spring 231 may be disposed externally to the reservoir 210. In another embodiment, the spring 231 may be disposed or encapsulated within the wall of reservoir 210. The spring 231 may be configured to apply a longitudinal expansion force to the reservoir 210 such that the spring 231 forces the folds 232 to separate from one another as the reservoir 210 is expanded from the collapsed state to the expanded state.

In use, the drainage system 200 may be provided to a user in the collapsed state to decrease shipping volume. The system 200 may also optionally be packaged or configured to comprise a vacuum when in the collapsed state. For instance, the reservoir 210 can be placed in the collapsed state and air and/or fluid can be evacuated from the reservoir 210. When ready to use, the drainage system 200 may be coupled to the drainage tube 202, which can include a tubing clamp 201 in a closed state. The distal end cap 212 and the proximal end cap 225 may be decoupled (e.g. rotated relative to one another) to release the vacuum generating member 230 and allow the spring 231 to force the reservoir 210 into the expanded state as illustrated in FIG. 6. As the reservoir 210 expands, a vacuum pressure is generated within the drainage system 200. The tubing clamp 201 may be opened to initiate flow (e.g., a higher pressure at a drainage site can cause the drainage fluid to flow from the patient to the vacuum pressured reservoir 210). In another embodiment, the reservoir 210 can be transitioned to the expanded state to generate a vacuum, after which a penetrating member at the end of the drainage tube 202 can be forced or pierced through a seal in the inlet port 213 to initiate drainage. And in yet another embodiment, a tubing clamp 201 is not used, and flow can be initiated as the vacuum generating member 230 is activated.

Figure 7:
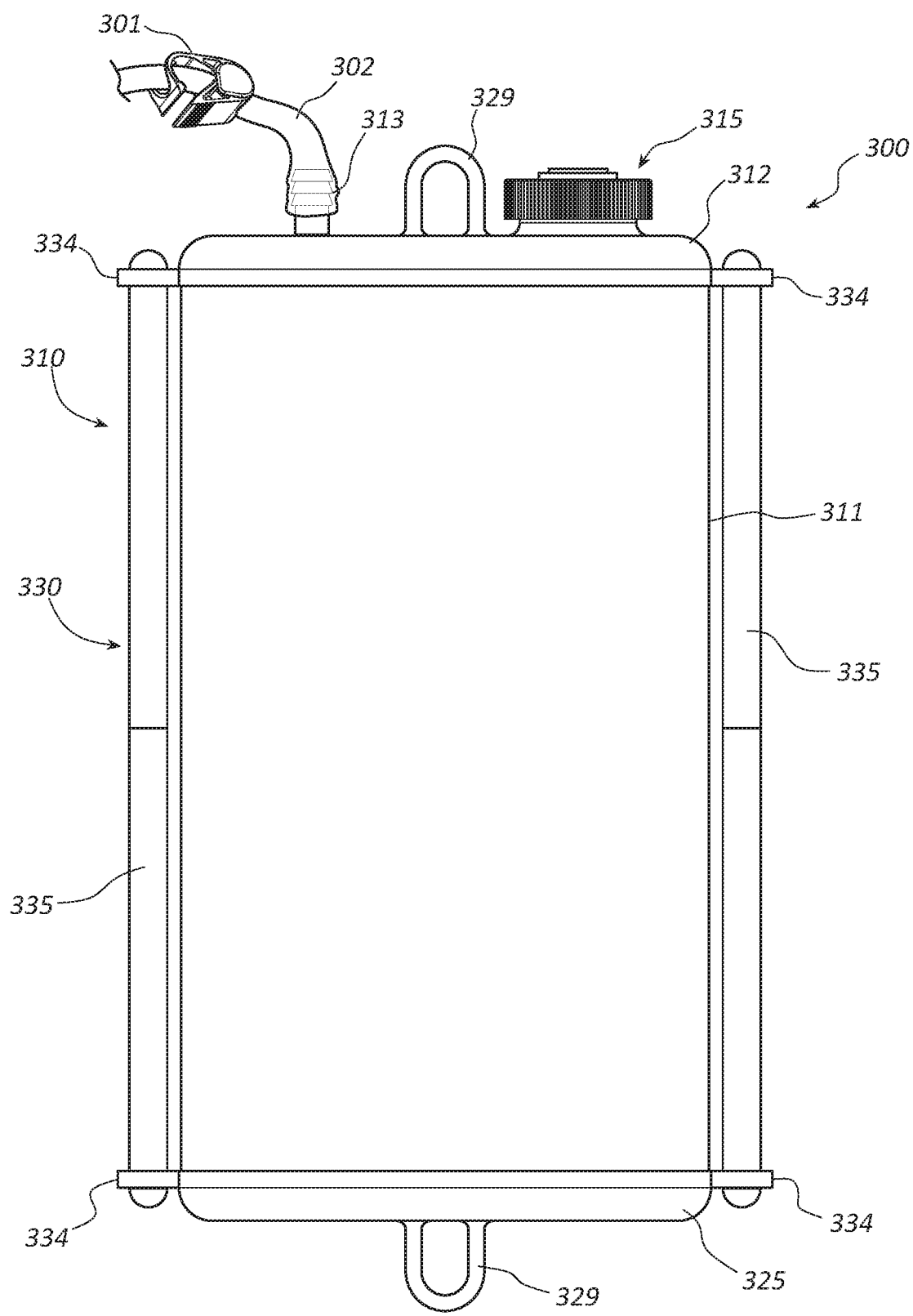
FIG. 7 is a side view of a vacuum assisted drainage system with external supports.

FIG. 7 depicts a side view of another embodiment of a drainage system 300. As depicted, the drainage system 300 includes a reservoir 310 and a vacuum generating member 330. The reservoir 310 has a compliant walled housing 311, a proximal end cap 325, and a distal end cap 312. The distal end cap 312 includes an inlet port 313 and a vent valve 315. The proximal and distal end caps 325, 312 include laterally extending flanges 334. The flange 334 may include a receptacle configured to receive a support 335. The proximal and distal end caps 325, 312 may include pull rings or tabs or straps 329 configured to facilitate longitudinal expansion of the reservoir 310 by a user. A drainage tube 302 is shown coupled to the inlet port 313 and a tubing clamp 301 is coupled to the drainage tube 302. A drainage tube 302 having a penetrating member or tip can also be used with an inlet port 313 having a seal.

The vacuum generating member 330 includes the support 335 configured to support the reservoir 310 in an expanded state with the housing 311 longitudinally taut. This prevents the housing 311 from collapsing radially inward and/or longitudinally when the reservoir 310 contains a vacuum pressure. Collapsing of the housing 311 could result in a decrease of volume and vacuum pressure. The support 335 may include a continuous rod and end nipples configured to be received by the receptacle of the flange 334. In some embodiments the support 335 may include a rod composed of at least two segments. The support 335 may be formed from any suitable rigid material, such as metal, plastics, polycarbonate, etc. The number of supports 335 may be two, three, four, five, or more.

In use, the drainage system 300 may be provided to the user in the collapsed state to decrease shipping volume. The system 300 may also optionally be packaged or configured to comprise a vacuum when in the collapsed state. For instance, the reservoir 310 can be placed in the collapsed state and air and/or fluid can be evacuated from the reservoir 310. When ready to use, the drainage system 300 may be coupled to the drainage tube 302, which can include a tubing clamp 301 in a closed state. The distal end cap 312 and the proximal end cap 325 may be decoupled (e.g. rotated relative to one another) to allow the clinician to longitudinally expand the reservoir 310 by gripping the pull rings 329 and longitudinally separating the proximal and distal end caps 325, 312. In other embodiments, the proximal and distal end caps 325, 312 are not coupled and need not be decoupled. As the reservoir 310 is expanded by the user, the volume of the reservoir 310 is increased and the pressure within the drainage system 300 is decreased. The supports 335 may be disposed between the flanges 334 of the distal end cap 312 and the proximal end cap 325 to maintain the reservoir 310 in the expanded state. The tubing clamp 301 may be opened to initiate flow (e.g., a higher pressure at the drainage site can cause the drainage fluid to flow from the patient to the vacuum pressured reservoir 310). In another embodiment, the reservoir 310 can be transitioned to the expanded state to generate a vacuum, after which a penetrating member at the end of the drainage tube 302 can be forced or pierced through a seal in the inlet port 313 to initiate drainage. And in yet another embodiment, a tubing clamp 301 is not used, and flow can be initiated as the vacuum generating member 330 is activated.

Figure 8:
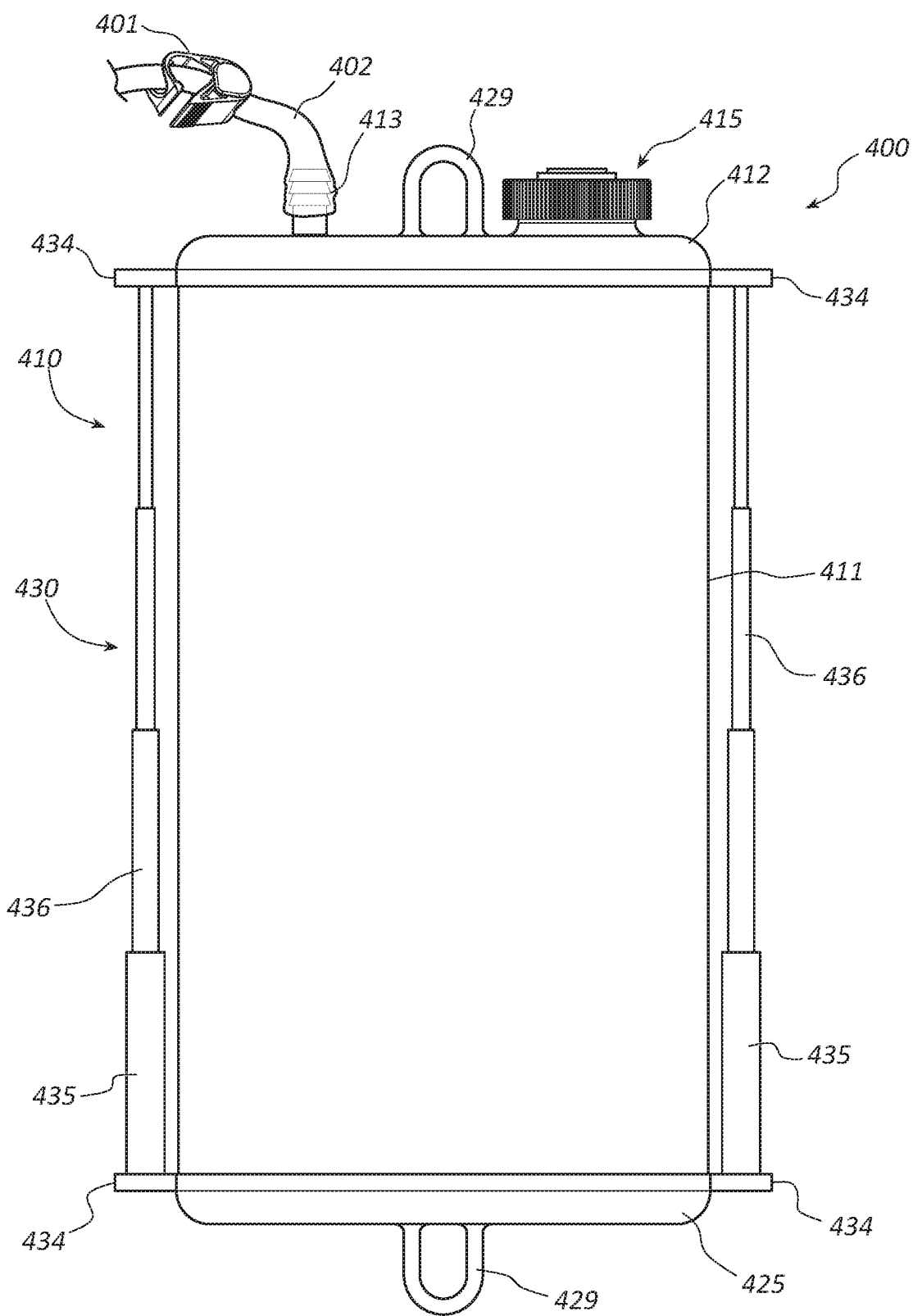
FIG. 8 is a side view of a vacuum assisted drainage system with telescoping external supports.

FIG. 8 depicts a side view of another embodiment of a drainage system 400. As depicted, the drainage system 400 includes a reservoir 410 and a vacuum generating member 430. The reservoir 410 has a compliant walled housing 411, a proximal end cap 425, and a distal end cap 412. The distal end cap 412 includes an inlet port 413 and a vent valve 415. The proximal and distal end caps 425, 412 include laterally extending flanges 434. The flange 434 may include a receptacle configured to receive a telescoping support 435. The proximal and distal end caps 425, 412 may include pull rings or tabs or straps 429 configured to facilitate longitudinal expansion of the reservoir 410 by a user. A drainage tube 402 is shown coupled to the inlet port 413 and a tubing clamp 401 is coupled to the drainage tube 402. A drainage tube 402 having a penetrating member or tip can also be used with an inlet port 413 having a seal.

The vacuum generating member 430 includes the telescoping support 435 configured to support the reservoir 410 in an expanded state with the housing 411 longitudinally taut. This prevents the housing 411 from collapsing radially inward and/or longitudinally when the reservoir 410 contains a vacuum pressure. Collapsing of the housing 411 could result in a decrease of volume and vacuum pressure. The telescoping support 435 may or may not be fixedly disposed in the receptacle of the flange 434. The telescoping support 435 includes a plurality of coaxially aligned segments 436. A segment 436 may be extendable from an adjacent segment 436 and configured to lockingly engage with the adjacent segment 436 in a telescoped state. The support 435 may be disposed within or external to the reservoir 410. The number of telescoping supports 435 may be two, three, four, five, or more.

In use, the drainage system 400 may be provided to a clinician in the collapsed state to decrease shipping volume. The system 400 may also optionally be packaged or configured to comprise a vacuum when in the collapsed state. For instance, the reservoir 410 can be placed in the collapsed state and air and/or fluid can be evacuated from the reservoir 410. When ready to use, the drainage system 400 may be coupled to the drainage tube 402, which can comprise a tubing clamp 401 in a closed state. The distal end cap 412 and the proximal end cap 425 may be decoupled (e.g. rotated relative to one another) to allow the clinician to longitudinally expand the reservoir 410 and the telescoping supports 435 by gripping the pull rings 429 and longitudinally separating the proximal and distal end caps 425, 412. In other embodiments, the proximal and distal end caps 425, 412 are not coupled and need not be decoupled. As the reservoir 410 and the vacuum generating member 430 are expanded by the user, a vacuum pressure is generated within the drainage system 400 and the telescoping supports 435 are configured to lock in a telescoped state to maintain the reservoir 410 in the expanded state. The tubing clamp 401 may be opened to initiate flow (e.g., a higher pressure at a drainage site can cause the drainage fluid to flow from the patient to the vacuum pressured reservoir 410). In another embodiment, the reservoir 410 can be transitioned to the expanded state to generate a vacuum, after which a penetrating member at the end of the drainage tube 402 can be forced or pierced through a seal in the inlet port 413 to initiate drainage. And in yet another embodiment, a tubing clamp 401 is not used, and flow can be initiated as the vacuum generating member 430 is activated.

Figure 9:
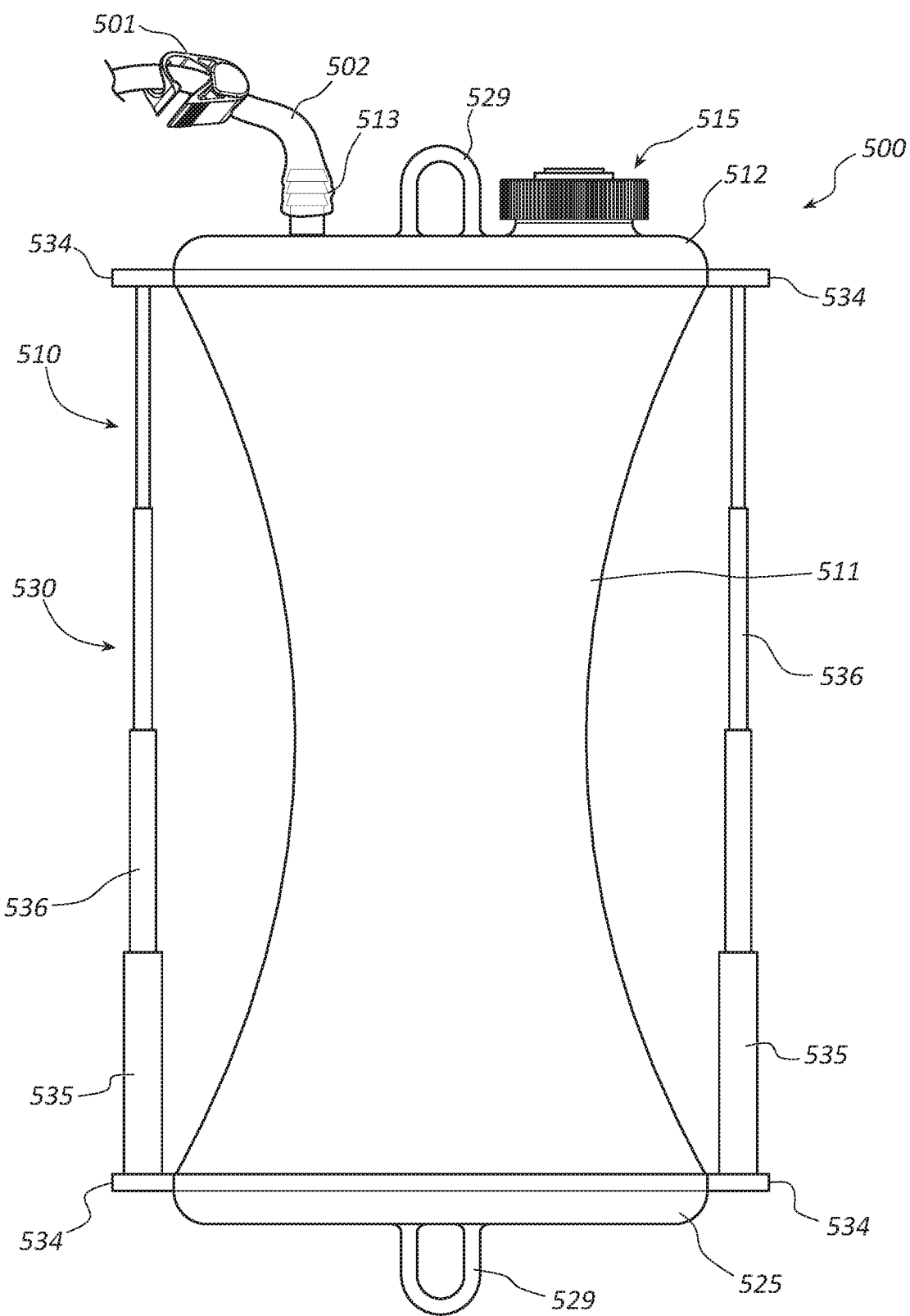
FIG. 9 is a side view of a vacuum assisted drainage system with an elastomeric housing and telescoping supports.

FIG. 9 depicts a side view of another embodiment of a drainage system 500. As depicted, the drainage system 500 includes a reservoir 510 and a vacuum generating member 530. The reservoir 510 has an elastomeric walled housing 511, a proximal end cap 525, and a distal end cap 512. The housing 511 may be formed of any suitable elastomeric material, such as silicone, silicone rubber, polyurethane, thermoplastic elastomer, etc. The distal end cap 512 includes an inlet port 513 and a vent valve 415. The proximal and distal end caps 525, 512 include laterally extending flanges 534. The flange 534 may include a receptacle configured to receive a telescoping support 535. The proximal and distal end caps 525, 512 may include pull rings or tabs or straps 529 configured to facilitate longitudinal expansion of the reservoir 510 by a user. A drainage tube 502 is shown coupled to the inlet port 513 and a tubing clamp 501 is coupled to the drainage tube 502. The number of telescoping supports 535 may be two, three, four, five, or more.

The vacuum generating member 530 includes the telescoping support 535 configured to support the reservoir 510 in an expanded state with the housing 511 stretched longitudinally. The support 535 may or may not be fixedly disposed in the receptacle of the flange 534. The support 535 includes a plurality of coaxially aligned segments 536. A segment 536 may be extendable from an adjacent segment 536 and configured to lockingly engage with the adjacent segment 536 in a telescoped state. The support 535 may be disposed external to the reservoir 510.

In use, the drainage system 500 may be provided to a clinician in the collapsed state to decrease shipping volume. The system 500 may also optionally be packaged or configured to comprise a vacuum when in the collapsed state. For instance, the reservoir 510 can be placed in the collapsed state and air and/or fluid can be evacuated from the reservoir 510. When ready to use, the drainage system 500 may be coupled to the drainage tube 502, which can comprise a tubing clamp 501 in a closed state. The distal end cap 512 and the proximal end cap 525 may be decoupled (e.g. rotated relative to one another) to allow the clinician to longitudinally expand the reservoir 510 (by stretching the housing 511) and the telescoping supports 535 by gripping the pull rings 529 and longitudinally separating the proximal and distal end caps 525, 512. In other embodiments, the proximal and distal end caps 525, 512 are not coupled and need not be decoupled. As the reservoir 510 and the vacuum generating member 530 are expanded by the user, a vacuum pressure is generated within the drainage system 500 and the telescoping supports 535 are configured to lock in a telescoped state to maintain the reservoir 510 in the expanded state. The tubing clamp 501 may be opened to initiate flow (e.g., a higher pressure at a drainage site can cause the drainage fluid to flow from the patient to the vacuum pressured reservoir 510). In another embodiment, the reservoir 510 can be transitioned to the expanded state to generate a vacuum, after which a penetrating member at the end of the drainage tube 502 can be forced or pierced through a seal in the inlet port 513 to initiate drainage. And in yet another embodiment, a tubing clamp 501 is not used, and flow can be initiated as the vacuum generating member 530 is activated.

Figure 10A:
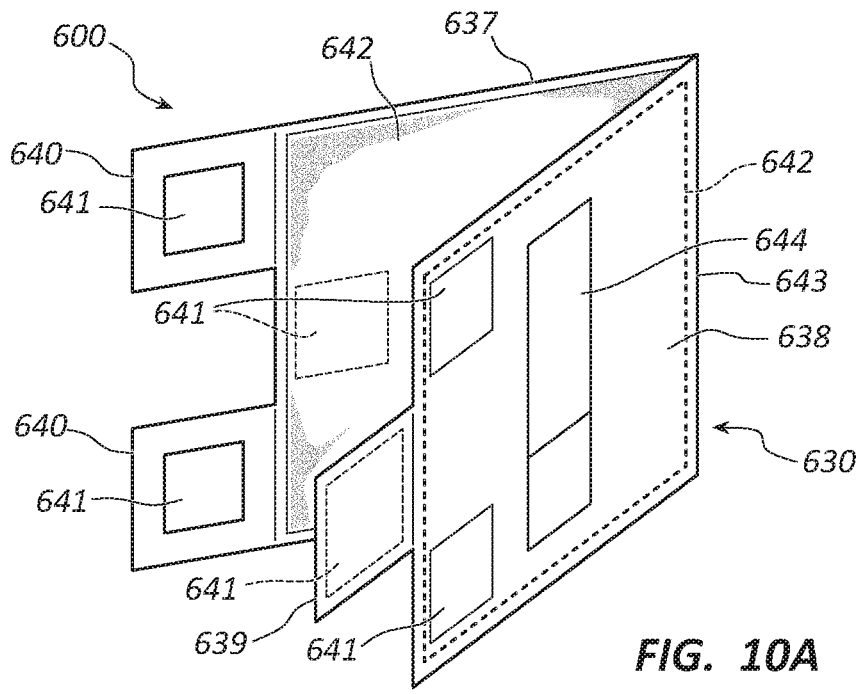
FIG. 10A is a perspective view of a vacuum assisted drainage system with a hinge.
Figure 10B:
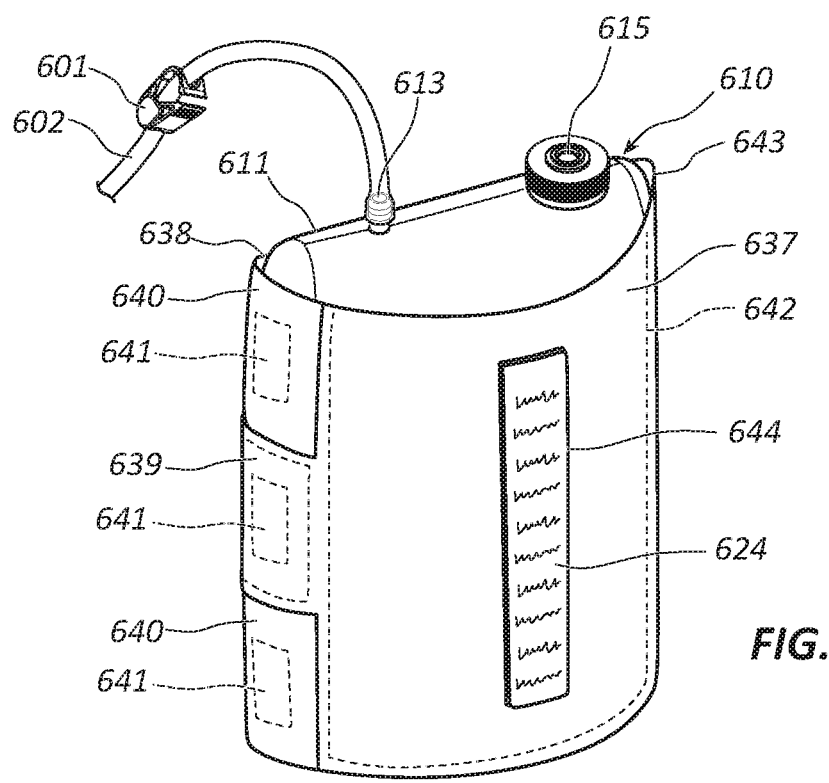
FIG. 10B is a perspective view of the vacuum assisted drainage system of FIG. 10A in an expanded state.

FIGS. 10A-10B depict another embodiment of a drainage system 600. As depicted the drainage system 600 includes a reservoir 610 and a vacuum generating member 630. The reservoir 610 may be configured as a flexible bag 611 including an inlet port 613, a vent valve 615, and a volume indicium 624. A drainage tube 602 may be coupled to the inlet port 613 with a tubing clamp 601 coupled to the drainage tube 602. A drainage tube 602 having a penetrating member or tip can also be used with an inlet port 613 having a seal.

As illustrated in FIG. 10A, the vacuum generating member 630 may include a first plate 637, a second plate 638, and a first hinge 643 disposed between and coupling the first and second plates 637, 638. The first and second plates 637, 638 may be generally flat, have a rectangular, oval, round, square, or any other suitable shape, and be configured to flex longitudinally. The first and second plates 637, 638 may be formed from materials such as polypropylene, polyethylene, polycarbonate, or any other suitable semi-rigid, flexible material. The first and second plates 637, 638 and the hinge 643 may be formed from the same material. In other embodiments, the first and second plates 637, 638 may be formed from different materials where the first plate 637 is more flexible than the second plate 638. The first and second plates 637, 638 and the first hinge 643 may be formed as an integral unit such as a single material formed from a flat extrusion or die cut from a flat sheet. In another embodiment, the first and second plates 637, 638 and the first hinge 643 may be formed as separate components and coupled together using any suitable manufacturing technique, such as gluing, welding, over molding, etc.

As illustrated, the first plate 637 includes a laterally extending tab 639 disposed generally centrally along an edge opposite the first hinge 643. The first tab 639 may be configured to be foldable such that the first tab 639 folds over a portion of the second plate 638 when the first and second plates 637, 638 are adjacent one another. The first tab 639 comprises a securement member 641 disposed on one side that is configured to couple with the securement member 641 disposed on the second plate 638 such that the first plate 637 may be coupled to the second plate 638 along the edge opposite the first hinge 643. In some embodiments, the securement member 641 may be formed from a hook-and-hook, hook-and-loop material, adhesive, snap, etc. The first plate 637 has a width that is greater than a width of the second plate 638. The first plate 637 may include a window 644 configured to allow visualization of the volume indicium 624 of the reservoir 610. An adhesive layer 642 may be disposed over at least a portion of an inside surface of the first plate 637.

The second plate 638 is shown to include second tabs 640 extending laterally from an edge opposite the first hinge 643. In other embodiments, the second plate 638 may include a single tab. The second tab 640 may be configured to be foldable such that the second tab 640 folds over a portion of the first plate 637 when the first and second plates 637, 638 are adjacent one another. The second tab 640 comprises the securement member 641 disposed on one side that is configured to couple with the securement member 641 disposed on the first plate 637 such that the second plate 638 may be coupled to the first plate 637 along the edge opposite the first hinge 643. The second plate 638 has a width that is less than a width of the first plate 637. The adhesive layer 642 may be disposed over at least a portion of an inside surface of the second plate 638.

As shown in FIGS. 10A-10B, the first hinge 643 is disposed along edges of the first and second plates 637, 638 that are opposite the first and second tabs 639, 640. The first hinge 643 may be configured as a continuous hinge. For example, the hinge may be a living hinge, a piano hinge, butterfly hinge, etc. In other embodiments, the first hinge 643 may include a plurality of hinges disposed along the edges of the first and second plates 637, 638. The first hinge 643 may be configured to allow the vacuum generating member 630 to pivot from a collapsed state where the first and second plates 637, 638 are adjacent one another to an expanded state where the edges of the first and second plates 637, 638 opposite the first hinge 643 are separated from one another.

In use, the drainage system 600 may be provided to a user in the collapsed state to decrease shipping volume. The system 600 may also optionally be packaged or configured to comprise a vacuum when in the collapsed state. For instance, the reservoir 610 can be placed in the collapsed state and air and/or fluid can be evacuated from the reservoir 610. When ready to use, the reservoir 610 may be placed between the first and second plates 637, 638 and adhered to the adhesive layers 642. In other embodiments, the reservoir 610 may be provided to the user already disposed between the first and second plates 637, 638. In some embodiments, the reservoir 610 can be coupled to the first and second plates 637, 638 using other suitable techniques. For example, the reservoir 610 may be coupled by RF welding, heat welding, over molding, etc. In still other embodiments, the reservoir 610 may be formed as an integral part of the first and second plates 637, 638. For example, the reservoir may be formed by blow molding or thermoforming techniques. The drainage tube 602, optionally including the tubing clamp 601 in a closed state may be coupled to the inlet port 613. The first tab 639 may be folded over a portion of the second plate 638 and the second tabs 640 folded over a portion of the first plate 637 and secured to the securement members 641. Because the width of the first plate 637 is greater than the width of second plate 638 and the free edges of the first and second plates 637, 638 are secured by the folded tabs 639, 640 and securement members 641, the first plate 637 may flex outwardly away from the second plate 638. The flexing may displace opposite sides of the reservoir 610 away from each other, resulting in an increased reservoir volume and a vacuum pressure within the reservoir 610 as depicted in FIG. 10B. The tubing clamp 601 may be opened to initiate flow (e.g., a higher pressure at a drainage site can cause the drainage fluid to flow from the patient to the vacuum pressured reservoir 610). In another embodiment, the reservoir 610 can be transitioned to the expanded state to generate a vacuum, after which a penetrating member at the end of the drainage tube 602 can be forced or pierced through a seal in the inlet port 613 to initiate drainage. And in yet another embodiment, a tubing clamp 601 is not used, and flow can be initiated as the vacuum generating member 630 is activated.

Figure 11A:
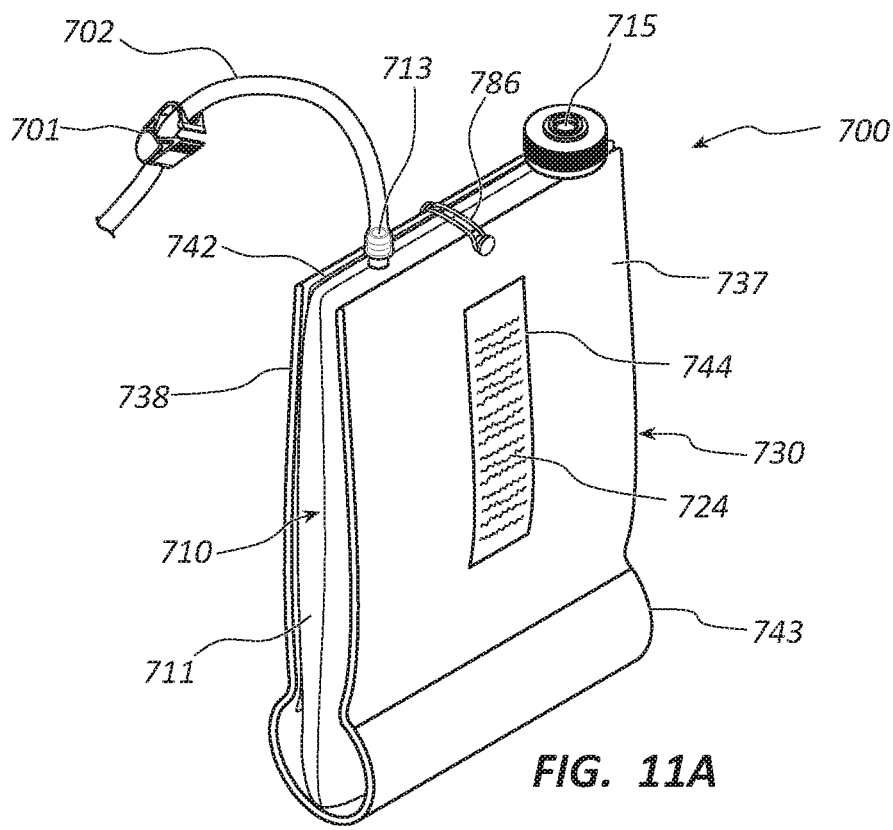
FIG. 11A is a perspective view of a vacuum assisted drainage system with another type of hinge.
Figure 11B:
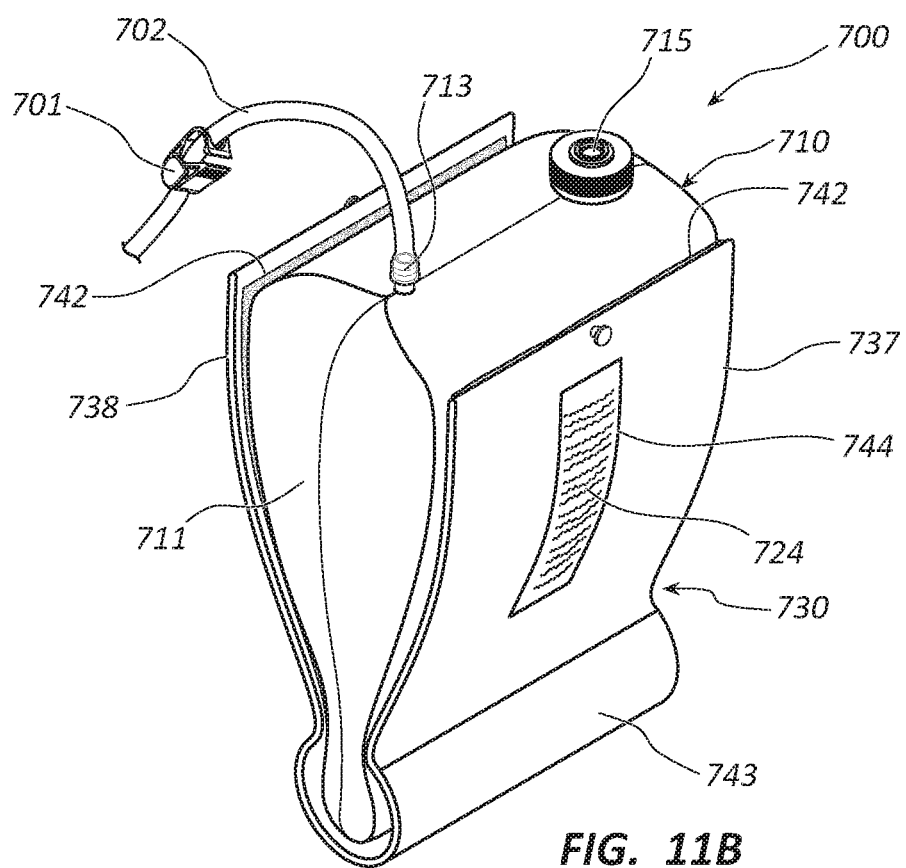
FIG. 11B is a perspective view of the vacuum assisted drainage system of FIG. 11A in an expanded state.

FIGS. 11A-11B depict another embodiment of a drainage system 700. As depicted, the drainage system 700 includes a reservoir 710 and a vacuum generating member 730. The reservoir 710 may be configured as a flexible bag 711 including an inlet port 713, a vent valve 715, and a volume indicium 724. A drainage tube 702 may be coupled to the inlet port 713 with a tubing clamp 701 coupled to the drainage tube 702. A drainage tube 702 having a penetrating member or tip can also be used with an inlet port 713 having a seal.

The vacuum generating member 730 may include a first plate 737, a second plate 738, and a first hinge 743 disposed between and coupled to the first and second plates 737, 738. The first and second plates 737, 738 may be generally flat or outwardly bowed and can have a rectangular, oval, round, square, or any other suitable shape. The first and second plates 737, 738 and the first hinge 743 may be formed as an integral unit. In another embodiment, the first and second plates 737, 738 and the first hinge 743 may be formed as separate components and coupled together using any suitable manufacturing technique, such as gluing, welding, over molding, etc. The first plate 737 may include a window 744 configured to allow visualization of the volume indicium 724 of the reservoir 710. An adhesive layer 742 may be disposed over at least a portion of an inside surface of the first and second plates 737, 738.

As shown in FIGS. 11A-11B, the first hinge 743 is disposed along edges of the first and second plates 737, 738. The first hinge 743 may be configured as a spring hinge that is biased to an open configuration. The first hinge 743 may be configured to allow the vacuum generating member 730 to bias from a collapsed state where the first and second plates 737, 738 are proximate one another to an expanded state where the edges of the first and second plates 737, 738 opposite the first hinge 743 are separated from one another.

In use, the drainage system 700 may be provided to a clinician in the collapsed state to decrease shipping volume. The system 700 may also optionally be packaged or configured to comprise a vacuum when in the collapsed state. For instance, the reservoir 710 can be placed in the collapsed state and air and/or fluid can be evacuated from the reservoir 710. When ready to use, a clip or band 786 around the vacuum generating member 730 configured to retain the vacuum generating member 730 in the collapsed state may be removed to allow the vacuum generating member 730 to expand to the expanded state. The reservoir 710 may be placed between the first and second plates 737, 738 and adhered to the adhesive layers 742. The vacuum generating member 730 may be moved to the collapsed state. In other embodiments, the reservoir 710 may be provided to the clinician already disposed between the first and second plates 737, 738. In some embodiments, the reservoir 710 can be coupled to the first and second plates 737, 738 using other suitable techniques. For example, the reservoir 710 may be coupled by RF welding, heat welding, over molding, etc. In still other embodiments, the reservoir 710 may be formed as an integral part of the first and second plates 737, 738. For example, the reservoir may be formed by blow molding or thermoforming techniques. The drainage tube 702, optionally including the tubing clamp 701 in a closed state, may be coupled to the inlet port 713. The first hinge 743 may bias the vacuum generating member 730 to the expanded state, therein expanding the volume of the reservoir 710 and generating a vacuum pressure within the reservoir 710 as illustrated in FIG. 10B. The tubing clamp 701 may be opened to initiate flow (e.g., a higher pressure at a drainage site can cause the drainage fluid to flow from the patient to the vacuum pressured reservoir 710). In another embodiment, the reservoir 710 can be transitioned to the expanded state to generate a vacuum, after which a penetrating member at the end of the drainage tube 702 can be forced or pierced through a seal in the inlet port 713 to initiate drainage. And in yet another embodiment, a tubing clamp 701 is not used, and flow can be initiated as the vacuum generating member 730 is activated.

Figure 12A:
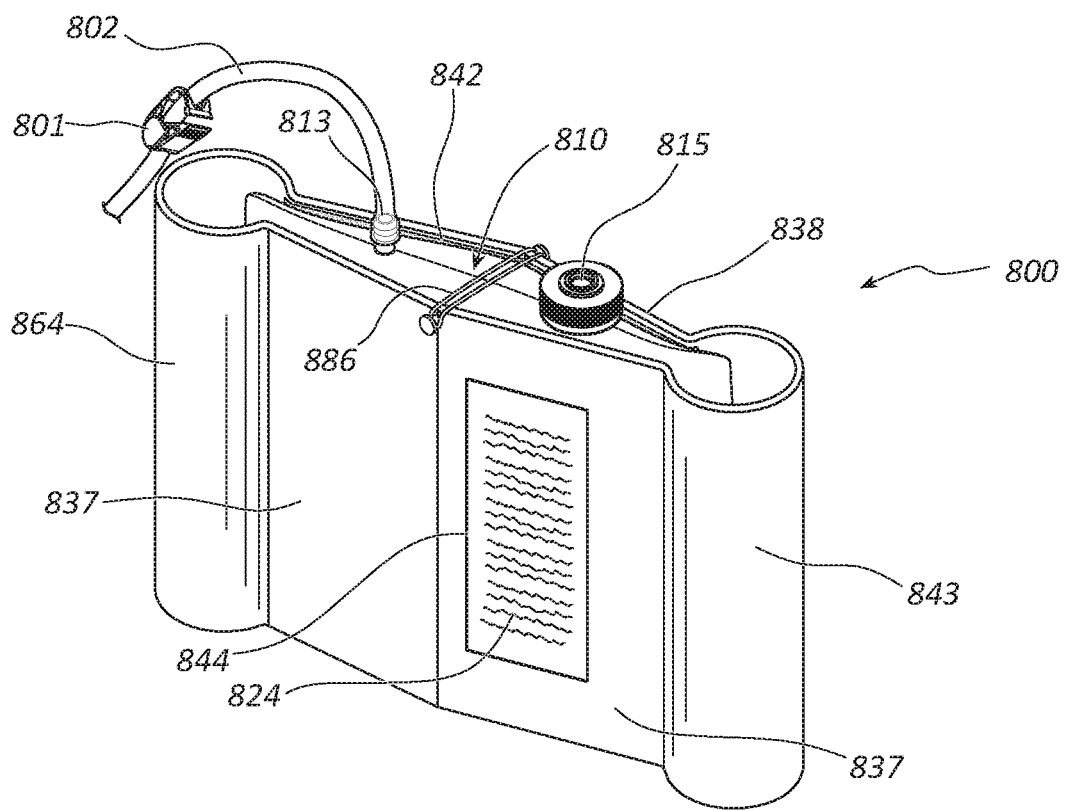
FIG. 12A is a perspective view of a vacuum assisted drainage system with another type of hinge.
Figure 12B:
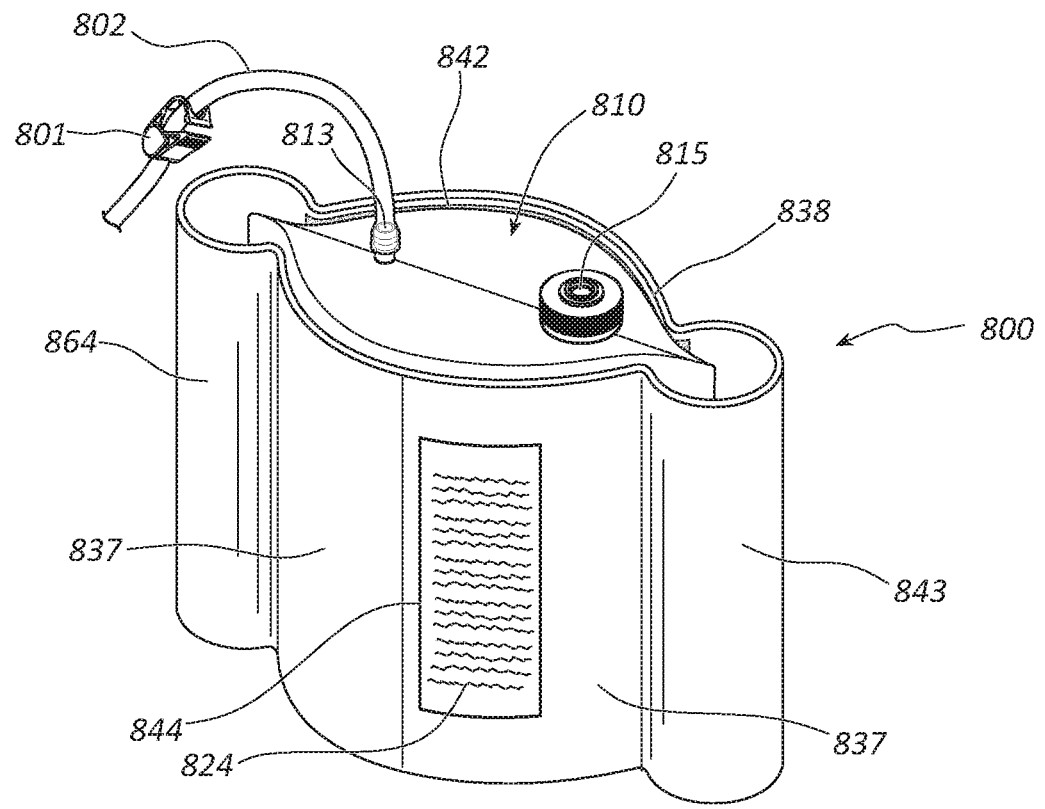
FIG. 12B is a perspective view of the vacuum assisted drainage system of FIG. 12A in an expanded state.

FIGS. 12A-12B depict another embodiment of a drainage system 800. As depicted the drainage system 800 can include a reservoir 810 and a vacuum generating member 830. The reservoir 810 may be configured as a flexible bag 811 including an inlet port 813, a vent valve 815, and a volume indicium 824.

The vacuum generating member 830 includes a first plate 837, a second plate 838, a first hinge 843, and a second hinge 864. The first and second hinges 843, 864 are disposed at opposite ends of and are coupled to the first and second plates 837, 838. The first and second plates 837, 838 may be flat or outwardly bowed and have a rectangular, oval, round, square, or any other suitable shape. The first and second plates 837, 838 and the first and second hinges 843, 864 may be formed as an integral unit. In another embodiment, the first and second plates 737, 738 and the first and second hinges 843, 864 may be formed as separate components and coupled together using any suitable manufacturing technique, such as gluing, welding, over molding, etc. The first plate 837 may include a window 844 configured to allow visualization of the volume indicium 824 of the reservoir 810. An adhesive layer 842 may be disposed over at least a portion of an inside surface of the first and second plates 837, 838.

As shown in FIGS. 12A-12B, the first hinge 843 is disposed along edges of the first and second plates 837, 838 and the second hinge 864 is disposed along opposite edges of the first and second plates 837, 838. The first and second hinges 843, 864 may be configured as spring hinges configured to bias the vacuum generating member 830 from the collapsed state where the first and second plates 837, 838 are proximate one another to the expanded state where the first and second plates 837, 838 are separated from one another at a central portion.

In use, the drainage system 800 may be provided to a clinician in the collapsed state to decrease shipping volume. The system 800 may also optionally be packaged or configured to comprise a vacuum when in the collapsed state. For instance, the reservoir 810 can be placed in the collapsed state and air and/or fluid can be evacuated from the reservoir 810. When ready to use, a clip or band 886 around the vacuum generating member 830 configured to retain the vacuum generating member 830 in the collapsed state may be removed to allow the vacuum generating member 830 to expand to the expanded state. The reservoir 810 may be placed between the first and second plates 837, 838 and adhered to the adhesive layers 842. The vacuum generating member 830 may be moved to the collapsed state. In other embodiments, the reservoir 810 may be provided to the clinician already disposed between the first and second plates 837, 838. In some embodiments, the reservoir 810 can be coupled to the first and second plates 837, 838 using other suitable techniques. For example, the reservoir 810 may be coupled by RF welding, heat welding, over molding, etc. In still other embodiments, the reservoir 810 may be formed as an integral part of the first and second plates 837, 838. For example, the reservoir may be formed by blow molding or thermoforming techniques. A drainage tube 802, optionally including a tubing clamp 801 in a closed state, may be coupled to the inlet port 813. The first and second hinges 843, 864 may bias the vacuum generating member 830 to the expanded state, therein expanding the volume of the reservoir 810 and generating a vacuum pressure within the reservoir 810. The tubing clamp 801 may be opened to initiate flow (e.g., a higher pressure at a drainage site can cause the drainage fluid to flow from the patient to the vacuum pressured reservoir 810). In another embodiment, the reservoir 810 can be transitioned to the expanded state to generate a vacuum, after which a penetrating member at the end of the drainage tube 802 can be forced or pierced through a seal in the inlet port 813 to initiate drainage. And in yet another embodiment, a tubing clamp 701 is not used, and flow can be initiated as the vacuum generating member 730 is activated.

Figure 13A:
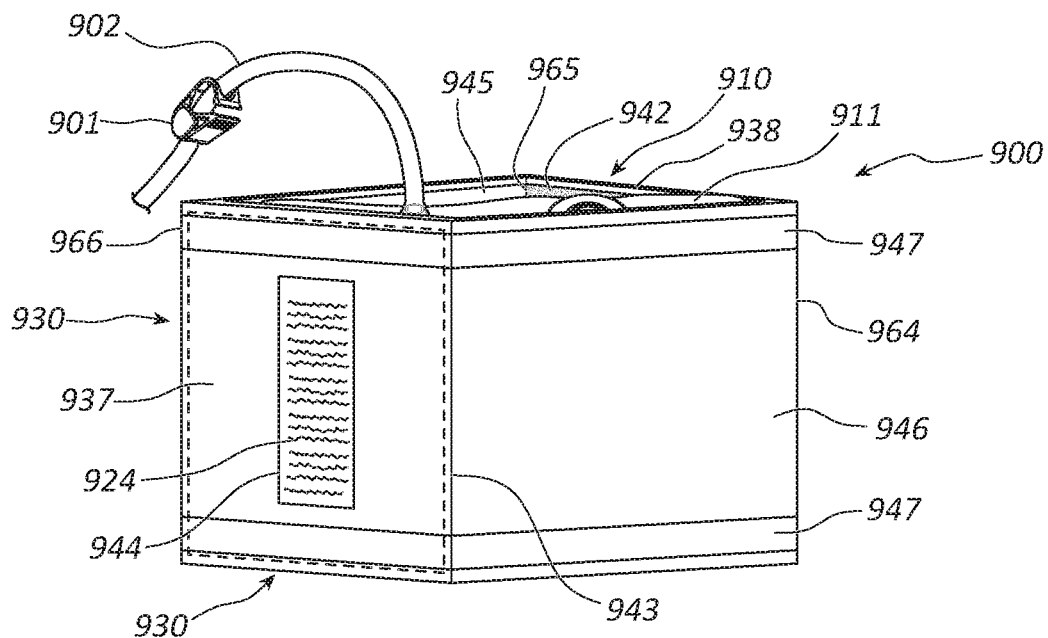
FIG. 13A is a perspective view of a vacuum assisted drainage system with another type of hinge.
Figure 13B:
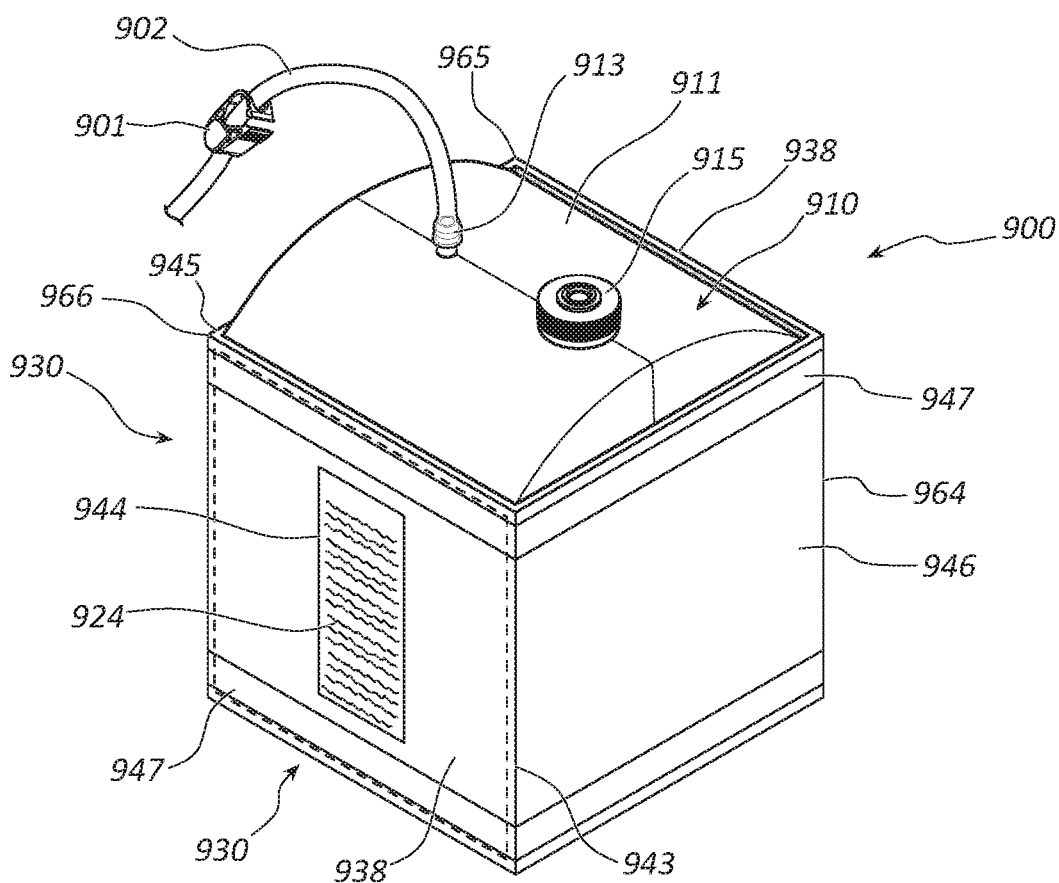
FIG. 13B is a perspective view of the vacuum assisted drainage system of FIG. 13A in an expanded state.

FIGS. 13A-13B depict another embodiment of a drainage system 900. As depicted, the drainage system 900 includes a reservoir 910 and a vacuum generating member 930. The reservoir 910 may be configured as a flexible bag 911 including an inlet port 913, a vent valve 915, and a volume indicium 924.

The vacuum generating member 930 may include a first plate 937, a second plate 938, a third plate 945, a fourth plate 946, a first hinge 943, a second hinge 964, a third hinge 965, and a fourth hinge 966. The first hinge 943 may be disposed between and coupled to the first plate 937 and the fourth plate 946. The second hinge 964 may be disposed between and coupled to the second plate 938 and the fourth plate 946. The third hinge 965 may be disposed between and coupled to the second plate 938 and the third plate 945. The fourth hinge 966 may be disposed between the first plate 937 and the third plate 965. The plates 937, 938, 945, 946 may be generally flat and have a rectangular or square shape. The plates 937, 938, 945, 946 and the hinges 943, 964, 965, 966 may be formed as an integral unit. In another embodiment, the plates 937, 938, 945, 946 and the hinges 943, 964, 965, 966 may be formed as separate components and coupled together using any suitable manufacturing technique, such as gluing, welding, over molding, etc. The first plate 937 may include a window 944 configured to allow visualization of the volume indicium 924 of the reservoir 910. An adhesive layer 942 may be disposed over at least a portion of an inside surface of the first and second plates 937, 938.

As shown in FIGS. 13A-13B, the first hinge 943 is disposed along edges of the first and fourth plates 937, 946, the second hinge 964 is disposed along ends of the second and fourth plates 938, 946, the third hinge 965 is disposed along ends of the second and third plates 938, 945, and the fourth hinge 966 is disposed along ends of the first and third plates 937, 945. The hinges 943, 964, 965, 966 may be configured as living hinges configured to allow the vacuum generating member 930 to move from the collapsed state where the plates 937, 938, 945, 946 are proximate one another to the expanded state where the plates 937, 938, 945, 946 are separated from one another.

The vacuum generating member 930 may include an elastomeric band 947 surrounding a perimeter. The elastomeric band 947 may be configured to apply a radially inward directed force at the second and fourth hinges 964, 966 such that the vacuum generating member 930 moves from the collapsed state as shown in FIG. 13A to the expanded state as shown in FIG. 13B. In other embodiments, the vacuum generating member 930 does not include the elastomeric band 947 and the vacuum generating member 930 is manually moved from the collapsed state to the expanded state by a user.

In use, the drainage system 900 may be provided to a clinician in the collapsed state to decrease shipping volume. The system 900 may also optionally be packaged or configured to comprise a vacuum when in the collapsed state. For instance, the reservoir 910 can be placed in the collapsed state and air and/or fluid can be evacuated from the reservoir 910. When ready to use, a clip or band (not shown) around the vacuum generating member 930, configured to retain the vacuum generating member 930 in the collapsed state, may be removed to allow the vacuum generating member 930 to expand to the expanded state. The reservoir 910 may be placed between the plates 937, 938, 945, 946 and adhered to the adhesive layers 942. In other embodiments, the reservoir 910 may be provided to the clinician already disposed between the plates 937, 938, 945, 946. In some embodiments, the reservoir 910 can be coupled to the plates 937, 938, 945, 946 using other suitable techniques. For example, the reservoir 910 may be coupled by RF welding, heat welding, over molding, etc. In still other embodiments, the reservoir 910 may be formed as an integral part of the plates 937, 938, 945, 946. For example, the reservoir may be formed by blow molding or thermoforming techniques. The vacuum generating member 930 may be moved to the collapsed state. A drainage tube 902, optionally including a tubing clamp 901 in a closed state, may be coupled to the inlet port 913. The elastomeric band 947 may bias the vacuum generating member 930 to the expanded state, therein expanding the volume of the reservoir 910 and generating a vacuum pressure within the reservoir 910 as illustrated in FIG. 13B. The tubing clamp 901 may be opened to initiate flow (e.g., a higher pressure at a drainage site can cause the drainage fluid to flow from the patient to the vacuum pressured reservoir 910). In another embodiment, the reservoir 910 can be transitioned to the expanded state to generate a vacuum, after which a penetrating member at the end of the drainage tube 902 can be forced or pierced through a seal in the inlet port 913 to initiate drainage. And in yet another embodiment, a tubing clamp 801 is not used, and flow can be initiated as the vacuum generating member 830 is activated.

Figure 14A:
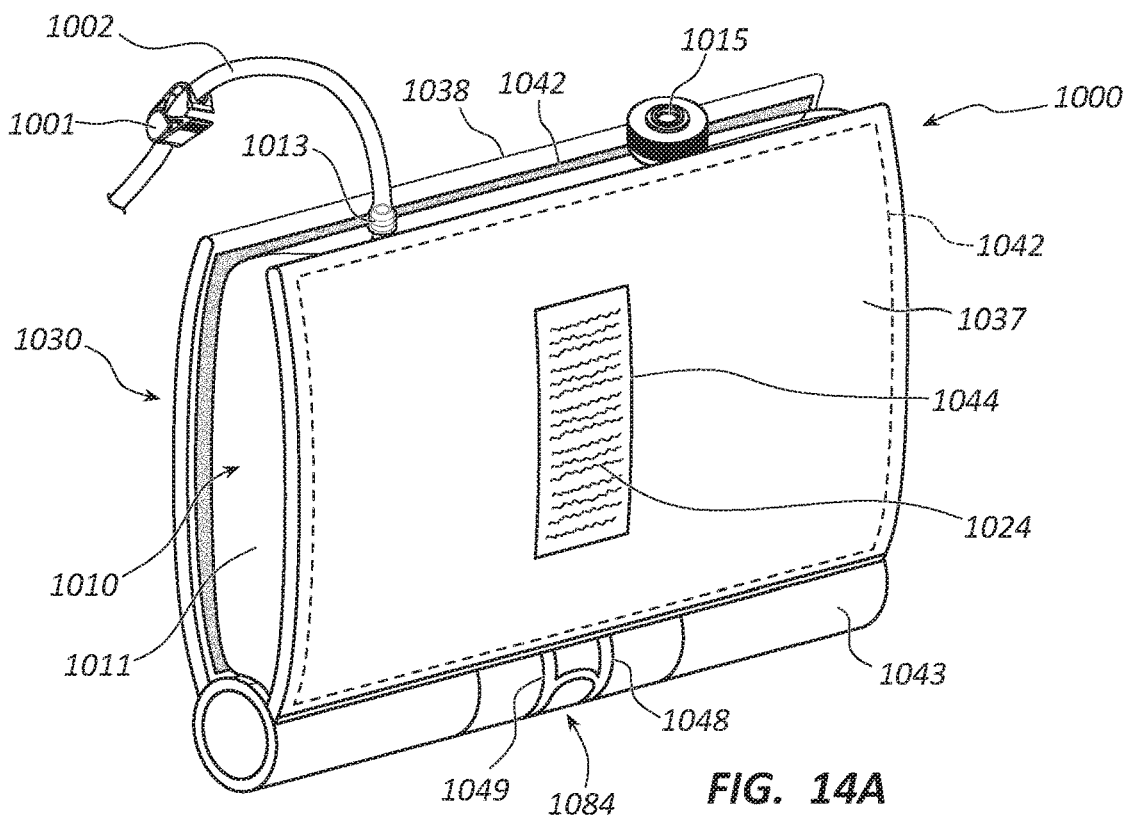
FIG. 14A is a perspective view of a vacuum assisted drainage system with a locking hinge.
Figure 14B:
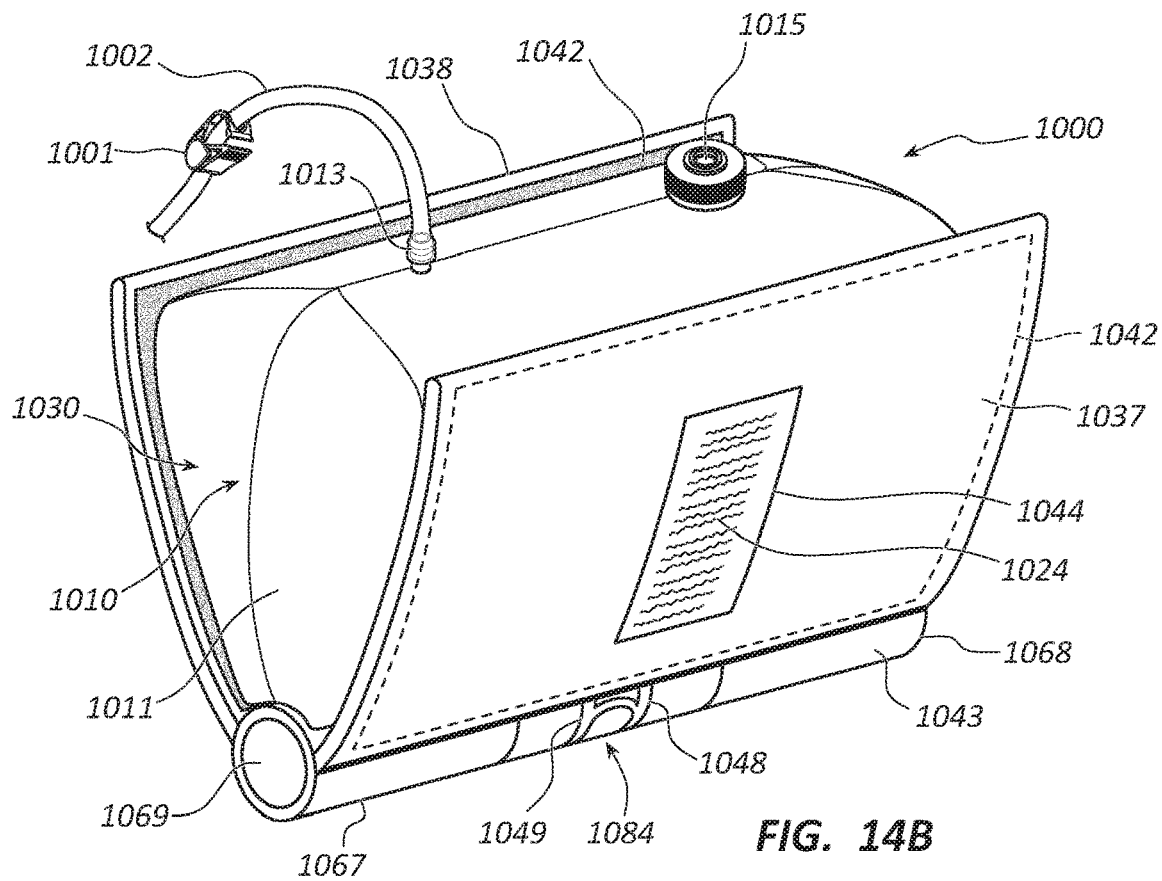
FIG. 14B is a perspective view of the vacuum assisted drainage system of FIG. 14A in an expanded state.

FIGS. 14A-14B depict another embodiment of a drainage system 1000. As depicted the drainage system 1000 can include a reservoir 1010 and a vacuum generating member 1030. The reservoir 1010 may be configured as a flexible bag 1011 including an inlet port 1013, a vent valve 1015, and a volume indicium 1024.

The vacuum generating member 1030 may include a first plate 1037, a second plate 1038, and a first hinge 1043 disposed between and coupled to the first and second plates 1037, 1038. The first and second plates 1037, 1038 may be generally flat or outwardly bowed and have a rectangular, oval, round, square, or any other suitable shape. The first and second plates 1037, 1038 and the first hinge 1043 may be formed as separate components and coupled together using any suitable manufacturing technique, such as gluing, welding, over molding, etc. The first plate 1037 may include a window 1044 configured to allow visualization of the volume indicium 1024 of the reservoir 1010. An adhesive layer 1042 may be disposed over at least a portion of an inside surface of the first and second plates 1037, 1038.

As shown in FIGS. 14A-14B, the first hinge 1043 is disposed along ends of the first and second plates 1037, 1038. The first hinge 1043 may be configured as a swivel hinge including a first segment 1067, a second segment 1068, and a swivel pin 1069. The first segment 1067 may be configured to swivel or rotate about the swivel pin 1069 relative to the second segment 1068. The first plate 1037 may be coupled to the first segment 1067 and the second plate 1038 may be coupled to the second segment 1068. The first hinge 1043 may be configured to allow the vacuum generating member 1030 to be moved from a collapsed state where the first and second plates 1037, 1038 are proximate one another to an expanded state where the ends of the first and second plates 1037, 1038 opposite the first hinge 1043 are separated from one another. The first hinge 1043 includes a locking member 1084. The locking member 1084 may include a detent 1048 disposed on the first segment 1067 configured to be engaged by a nub 1049 disposed on the second segment 1068 such that the vacuum generating member 1030 may be retained in an expanded state. In the expanded state the first plate 1037 may be disposed at an angle of about 10 degrees to about 60 degrees, from about 20 degrees to about 45 degrees, or about 30 degrees relative to the second plate 1038.

In use, the drainage system 1000 may be provided to a clinician in the collapsed state to decrease shipping volume. The system 1000 may also optionally be packaged or configured to comprise a vacuum when in the collapsed state. For instance, the reservoir 1010 can be placed in the collapsed state and air and/or fluid can be evacuated from the reservoir 1010. The vacuum generating member 1030 may be manually partially expanded and the reservoir 1010 may be placed between the first and second plates 1037, 1038 and adhered to the adhesive layers 1042. In other embodiments, the reservoir 1010 may be provided to the clinician already disposed between the first and second plates 1037, 1038. In some embodiments, the reservoir 1010 can be coupled to the first and second plates 1037, 1038 using other suitable techniques. For example, the reservoir 1010 may be coupled by RF welding, heat welding, over molding, etc. In still other embodiments, the reservoir 1010 may be formed as an integral part of the first and second plates 1037, 1038. For example, the reservoir may be formed by blow molding or thermoforming techniques. A drainage tube 1002, including a tubing clamp 1001 in a closed state, may be coupled to the inlet port 1013. The vacuum generating member 1030 may be manually expanded to the expanded state by separation of the free ends of the first and second plates 1037, 1038, therein expanding the volume of the reservoir 1010 and generating a vacuum pressure within the reservoir 1010 as depicted in FIG. 14B. In the expanded state the locking member 1084 of the first hinge 1043 may be rotatably locked such that the vacuum generating member 1030 is maintained in the expanded state. The tubing clamp 1001 may be opened to initiate flow (e.g., a higher pressure at a drainage site can cause the drainage fluid to flow from the patient to the vacuum pressured reservoir 1010). In another embodiment, the reservoir 1010 can be transitioned to the expanded state to generate a vacuum, after which a penetrating member at the end of the drainage tube 1002 can be forced or pierced through a seal in the inlet port 1013 to initiate drainage. And in yet another embodiment, a tubing clamp 1001 is not used, and flow can be initiated as the vacuum generating member 1030 is activated.

Figure 15A:
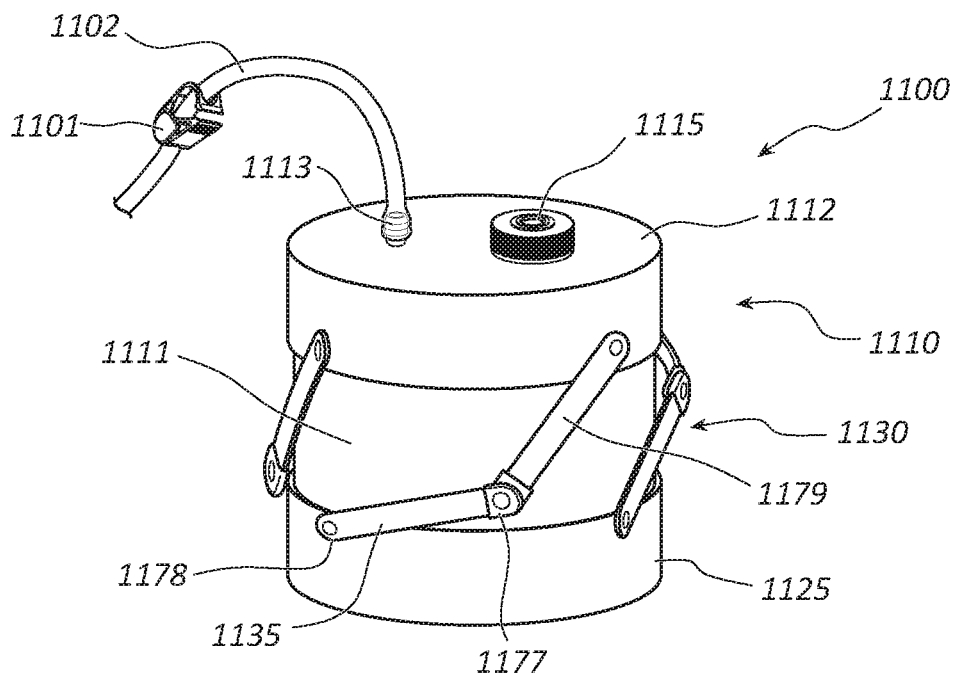
FIG. 15A is a perspective view of a vacuum assisted drainage system with a foldable support.
Figure 15B:
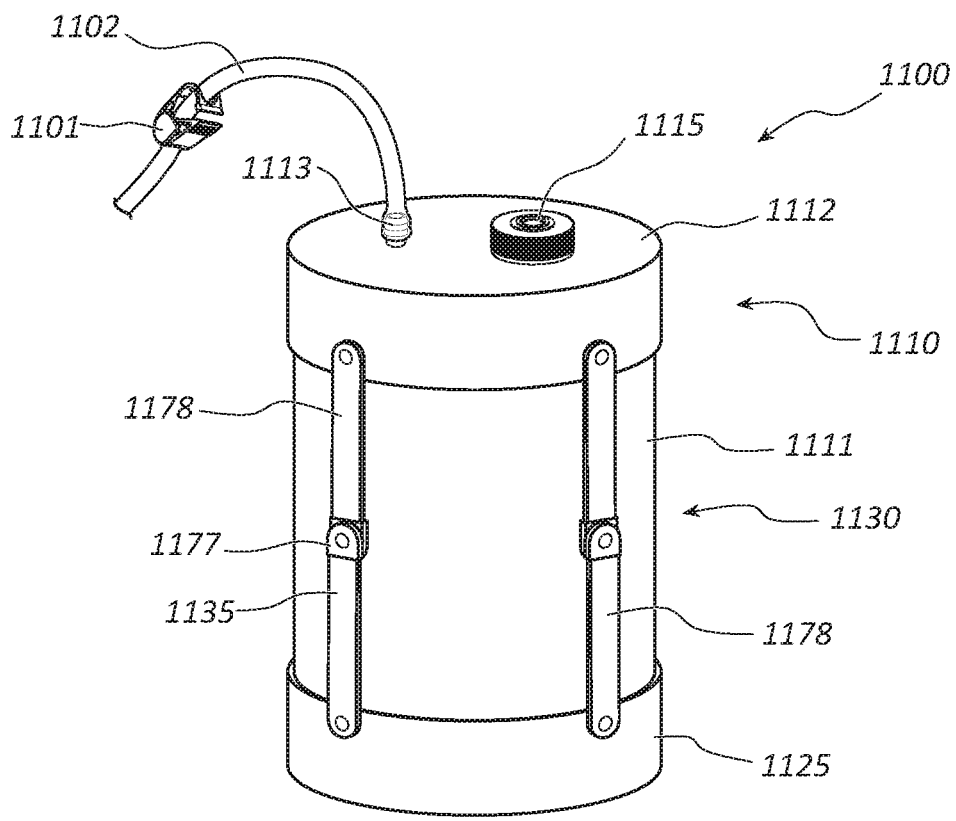
FIG. 15B is a perspective view of the vacuum assisted drainage system of FIG. 15A in an expanded state.

FIGS. 15A-15B depict another embodiment of a drainage system 1100. As depicted, the drainage system 1100 includes a reservoir 1110 and a vacuum generating member 1130. The reservoir 1110 includes a proximal end cap 1125, a distal end cap 1112, and a compliant walled housing 1111 coupled to the end caps 1112, 1125. The distal end cap 1112 includes an inlet port 1113 configured to be in fluid communication with the reservoir 1110 and a vent valve 1115. The drainage tube 1102 is coupled to the inlet port 1113 and a tubing clamp 1101 is coupled to the drainage tube 1102. A drainage tube 1102 having a penetrating member or tip can also be used with an inlet port 1113 having a seal.

The vacuum generating member 1130 includes a foldable support 1135 configured to support the reservoir 1110 in an expanded state. The foldable support 1135 includes a proximal segment 1178, a distal segment 1179, and a locking member 1177. The proximal segment 1178 is pivotably coupled to the proximal end cap 1125 and the distal segment 1179 is pivotably coupled to the distal end cap 1112. In the collapsed state, the pivot point of the proximal segment 1178 is circumferentially offset from the pivot point of the distal segment 1179. This circumferential offset may be about 45 degrees to about 150 degrees, about 60 degrees to about 130 degrees, or about 120 degrees. In other embodiments, the pivot point of the proximal segment 1178 may be longitudinally aligned with the pivot point of the distal segment 1179 in the collapsed state. The number of foldable supports 1135 may be three, four, five, or more. As shown in FIG. 15A, the distal and proximal segments 1178, 1179 form an angle when the vacuum generating member 1130 is in a collapsed state. The angle may range from about 30 degrees to about 150 degrees.

The locking member 1177 may be configured to allow the foldable support 1135 to pivotably move from a folded configuration when the vacuum generating member 1130 is in the collapsed state to a straight configuration when the vacuum generating member 1130 is in the expanded state. The locking member 1177 includes a locking mechanism that is configured to maintain the foldable support 1135 in the straight configuration. In the straight configuration, the foldable support 1135 is configured to maintain the reservoir 1110 in the expanded state where the housing 1111 is longitudinally taut to prevent the housing 1111 from collapsing radially inward and/or longitudinally, which could result in a decrease in volume and vacuum within the reservoir 1110.

In use, the drainage system 1100 may be provided to a clinician in the collapsed state to decrease shipping volume as illustrated in FIG. 15A. The system 1100 may also optionally be packaged or configured to comprise a vacuum when in the collapsed state. For instance, the reservoir 1110 can be placed in the collapsed state and air and/or fluid can be evacuated from the reservoir 1110. When ready to use, the drainage system 1100 may be coupled to the drainage tube 1102, which can comprise a tubing clamp 1101 in a closed state. The distal end cap 1112 and the proximal end cap 1125 may be rotated relative to one another and/or displaced longitudinally to expand the reservoir 1110 to an expanded state where the foldable support 1135 moves from the folded configuration to the straight and locked configuration as illustrated in FIG. 15B. In other embodiments, the distal end cap 1112 and the proximal end cap 1125 may be longitudinally displaced from one another without rotation. A vacuum pressure may be generated within the drainage system 1100 when the vacuum generating member 1130 is expanded from the collapsed state to the expanded state, therein increasing the volume of the reservoir 1110. The tubing clamp 1101 may be opened to initiate flow (e.g., a higher pressure at a drainage site can cause the drainage fluid to flow from the patient to the vacuum pressured reservoir 1110). In another embodiment, the reservoir 1110 can be transitioned to the expanded state to generate a vacuum, after which a penetrating member at the end of the drainage tube 1102 can be forced or pierced through a seal in the inlet port 1113 to initiate drainage. And in yet another embodiment, a tubing clamp 1101 is not used, and flow can be initiated as the vacuum generating member 1130 is activated.

Figure 16A:
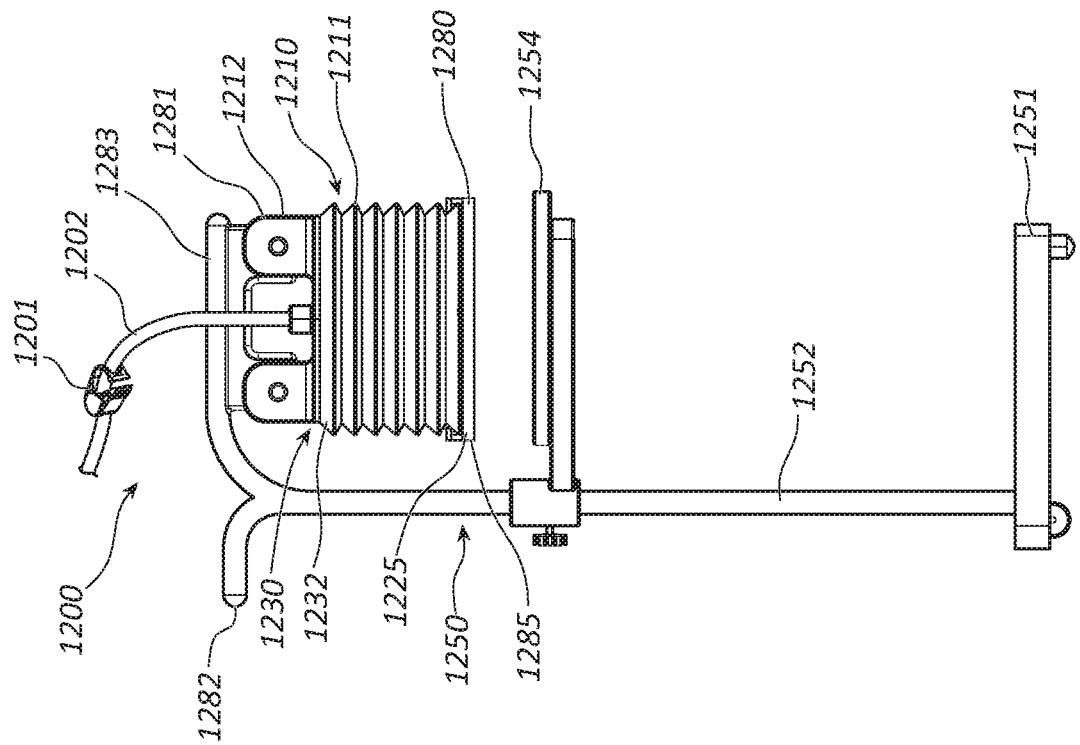
FIG. 16A is a side view of a vacuum assisted drainage system with a weight and stand.
Figure 16B:
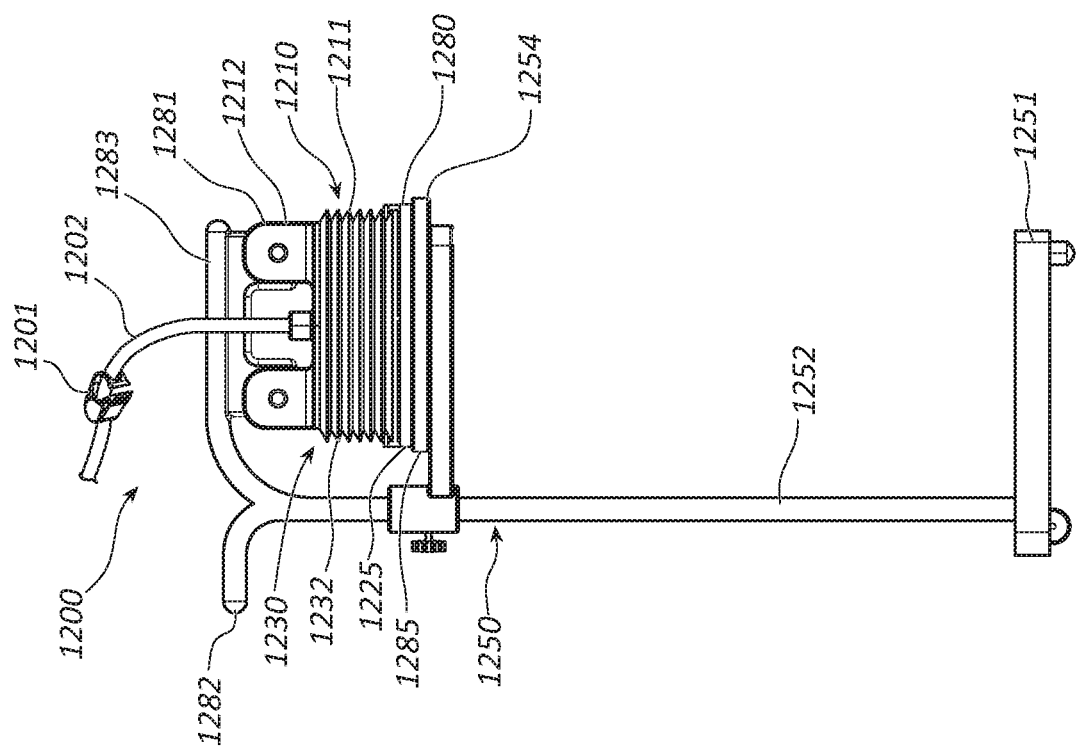
FIG. 16B is a side view of the vacuum assisted drainage system of FIG. 16A in an expanded state.

FIGS. 16A-16B depict another embodiment of a drainage system 1200. As depicted, the drainage system 1200 includes a reservoir 1210, a vacuum generating member 1230, and a support stand 1250. The reservoir 1210, as shown, includes a proximal end cap 1225, a distal end cap 1212, and a housing 1211 coupled to the proximal and distal end caps 1225, 1212. The housing 1211 includes a concertinaed wall configured to expand and collapse. In other words, the housing 1211 includes a wall having a series of folds 1232 configured to collapse upon one another when the drainage system 1200 is in a collapsed state, as depicted in FIG. 16A, and to separate from one another when the drainage system 1200 is in an expanded state, as depicted in FIG. 16B. The distal end cap 1212 includes an inlet port 1213 configured to be in fluid communication with the reservoir 1210 and a hanging support 1281. For example, in some embodiments the hanging support 1281 may be configured as a loop. A drainage tube 1202 is coupled to the inlet port 1213 and a tubing clamp 1201 is coupled to the drainage tube 1202. The proximal end cap 1225 can include a horizontally oriented pocket 1285 configured to receive a weight 1280. Other ways of coupling the weight 1280 to the proximal end cap 1225 are also contemplated.

As illustrated in FIGS. 16A-16B, the vacuum generating member 1230 includes the weight 1280 configured to expand the reservoir 1210 from the collapsed state to the expanded state and to generate a vacuum pressure within the drainage system 1200. The weight 1280 may be formed in a disc shape configured to be slidingly disposed within a pocket 1285 of the proximal end cap 1225. The weight 1280 may be formed from any suitable dense material. For example, the weight 1280 may be formed from steel, iron, lead, etc. The weight 1280 may have a mass of about one pound to about 20 pounds, about 5 pounds to about 15 pounds, and about 10 pounds. In another embodiment, the vacuum generating member 1230 may include a compression spring disposed within or external to the housing 1211. In such an embodiment, the compression spring may be configured to assist with the generation of the vacuum pressure.

The support stand 1250, as illustrated in FIGS. 16A-16B, includes a base 1251, a pole 1252, a platform 1254, a handle 1282, and a hanging support arm 1283. The base 1251 may comprise wheels configured to allow the support stand 1250 to be easily moved from one location to another by a user. The pole 1252 is vertically coupled to the base 1251. The platform 1254 is movably coupled to the pole 1252 and may include a clamp configured to allow the platform 1254 to be moved vertically relative to the pole 1252 by the user. The handle 1282 may be disposed adjacent an upper portion of the pole 1252. The handle 1282 may be configured to be grasped by the user when the support stand 1250 is moved. The hanging support arm 1283 may be disposed adjacent the upper portion of the pole 1252. The hanging support arm 1283 may extend horizontally from the pole 1252 and include a hanging support member (e.g., a hook) configured to couple with the hanging support 1281. The hanging support arm 1283 may be configured to support the drainage system 1200 such that the drainage system 1200 is suspended from the distal end cap 1212 and the proximal end cap 125 is not supported, allowing gravity to expand the drainage system 1200 in a downward direction. The support stand 1250 can also be configured to function as a cane, walker, or seat.

In use, the drainage system 1200 may be provided to a user in the collapsed state to decrease shipping volume as shown in FIG. 16A. The system 1200 may also optionally be packaged or configured to comprise a vacuum when in the collapsed state. For instance, the reservoir 1210 can be placed in the collapsed state and air and/or fluid can be evacuated from the reservoir 1210. When ready to use, the drainage system 1200 may be coupled to the drainage tube 1202, which can comprise a tubing clamp 1201 in a closed state. The drainage system 1200 may be loaded onto the loading platform 1254 where a height of the loading platform 1254 is set to allow the hanging support 1281 to be coupled to the hanging support arm 1283 and to support the proximal end cap 1225. The weight 1280 may be disposed into the pocket 1285 of proximal end cap 1225 or otherwise coupled to the proximal end cap 1225. The height of the loading platform 1254 may be adjusted downward to remove the support of the proximal end cap 1225 and allow the drainage system 1200 to be suspended from the hanging support arm 1283 as illustrated in FIG. 16B. As gravity pulls downward on the weight 1280, the reservoir 1210 may be longitudinally expanded downward and expanded such that a vacuum pressure may be generated within the drainage system 1200. The tubing clamp 1201 may be opened to initiate flow (e.g., a higher pressure at a drainage site can cause the drainage fluid to flow from the patient to the vacuum pressured reservoir 1210). In another embodiment, the reservoir 1210 can be transitioned to the expanded state to generate a vacuum, after which a penetrating member at the end of the drainage tube 1202 can be forced or pierced through a seal in the inlet port 1213 to initiate drainage. And in yet another embodiment, a tubing clamp 1201 is not used, and flow can be initiated as the vacuum generating member 1230 is activated.

Figure 17B:
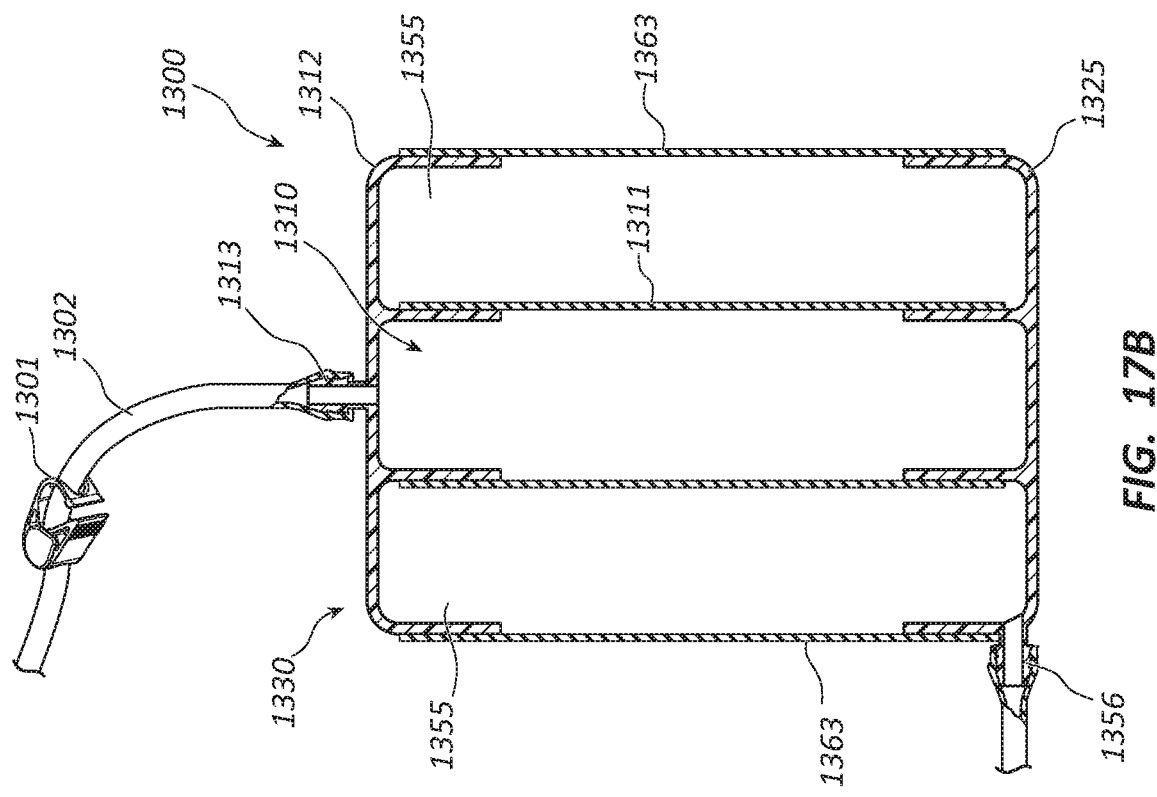
FIG. 17B is a cross-sectional view of the vacuum assisted drainage system of FIG. 17A in an expanded state.
Figure 17A:
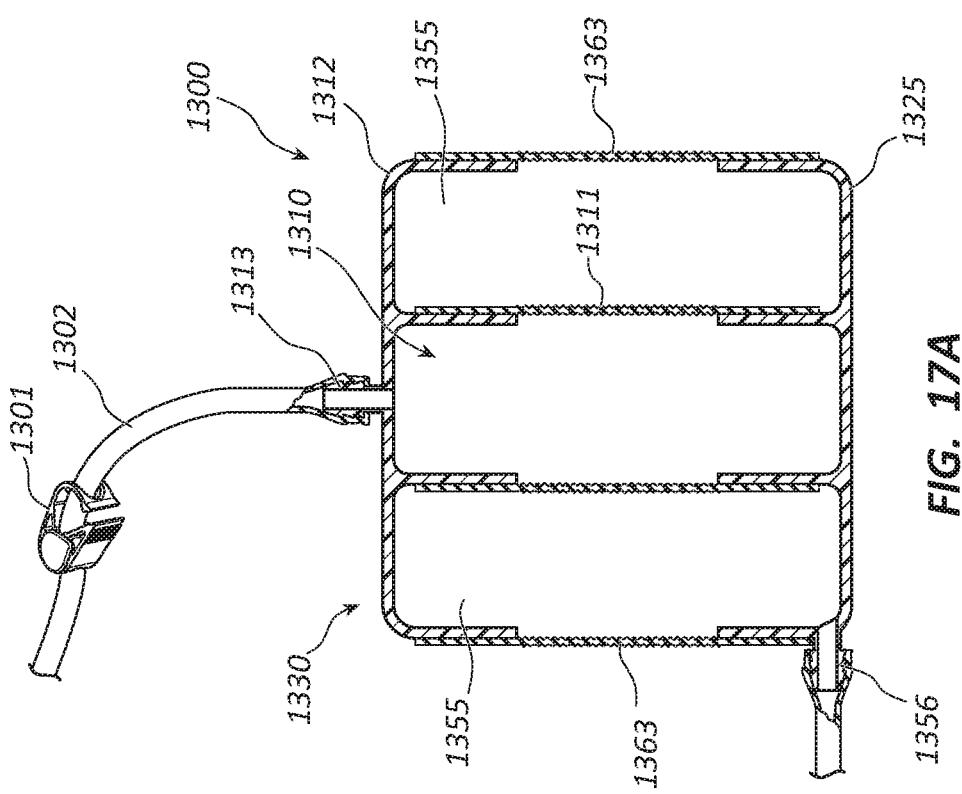
FIG. 17A is a cross-sectional view of a vacuum assisted drainage system with an expansion chamber in a collapsed state.

FIGS. 17A-17B illustrate another embodiment of a drainage system 1300. As illustrated the drainage system 1300 includes a reservoir 1310 and a vacuum generating member 1330. The reservoir 1310 includes a proximal end cap 1325, a distal end cap 1312, and a compliant walled housing 1311 coupled to the end caps 1312, 1325. The distal end cap 1312 includes an inlet port 1313 configured to be in fluid communication with the reservoir 1310. A drainage tube 1302 is coupled to the inlet port 1313 and a tubing clamp 1301 is coupled to the drainage tube 1302. A drainage tube 1302 having a penetrating member or tip can also be used with an inlet port 1313 having a seal.

The vacuum generating member 1330 includes a compliant outer wall 1363 defining an expansion chamber 1355 configured to at least partially surround the reservoir 1310. In other embodiments. The expansion chamber 1355 is surrounded by the reservoir 1310. In some embodiments, the expansion chamber 1355 may include a plurality of chambers or enclosed channels in fluid communication with one another. The compliant outer wall 1363 is coupled to the end caps 1312, 1325. The expansion chamber 1355 is fluidly isolated from the reservoir 1310. The expansion chamber 1355 may be configured to be filled with a pressurized gas, such as carbon dioxide, nitrogen, air, etc. Filling of the expansion chamber 1355 with a pressurized gas may cause the expansion chamber 1355 to expand from a collapsed state, as shown in FIG. 17A, to an expanded state, as shown in FIG. 17B. In other embodiments, the expansion chamber 1355 may be configured to be filled with an expandable material, such as hydrogel, configured to swell and expand the expansion chamber 1355 when exposed to a fluid, such as water.

In use, the drainage system 1300 may be provided to a clinician in the collapsed state to decrease shipping volume The system 1300 may also optionally be packaged or configured to comprise a vacuum when in the collapsed state. For instance, the reservoir 1310 can be placed in the collapsed state and air and/or fluid can be evacuated from the reservoir 1310. When ready to use, the inlet port 1313 may be coupled to the drainage tube 1302, which can comprise a tubing clamp 1301 in a closed state. A fill port 1356 may be coupled to a source of pressurized gas and the expansion chamber 1355 filled with the pressurized gas such that the expansion chamber 1355 and the reservoir 1310 are longitudinally expanded to the expanded state as depicted in FIG. 17B. As the reservoir 1310 is expanded, a volume of the reservoir 1310 is increased and a vacuum pressure may be generated within the reservoir 1310. The tubing clamp 1301 may be opened to initiate flow (e.g., a higher pressure at a drainage site can cause the drainage fluid to flow from the patient to the vacuum pressured reservoir 1310). In another embodiment, the reservoir 1310 can be transitioned to the expanded state to generate a vacuum, after which a penetrating member at the end of the drainage tube 1302 can be forced or pierced through a seal in the inlet port 1313 to initiate drainage. And in yet another embodiment, a tubing clamp 1301 is not used, and flow can be initiated as the vacuum generating member 1330 is activated.

Figure 18:
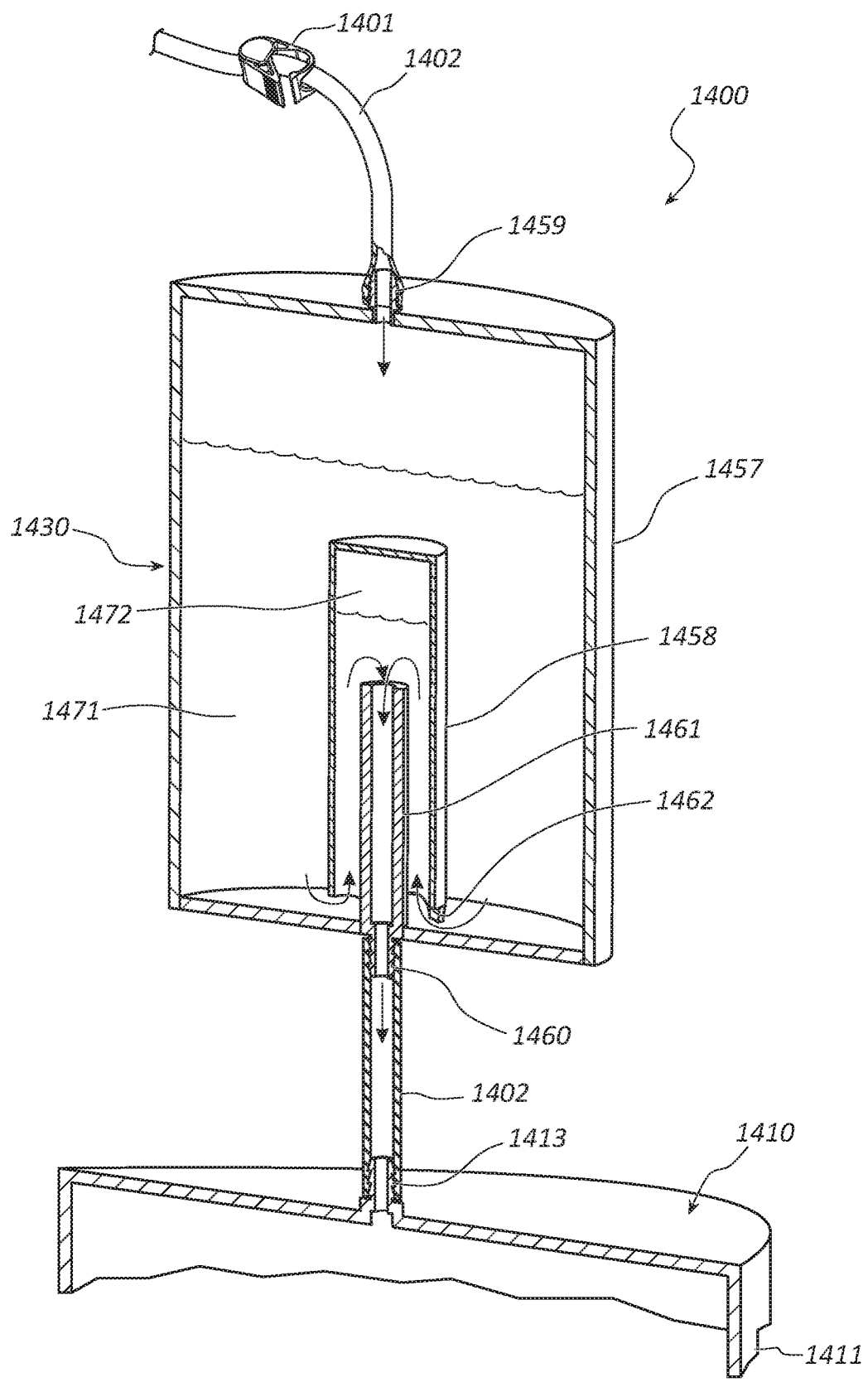
FIG. 18 is a perspective, cross-sectional view of a vacuum assisted drainage system with a siphon valve.

FIG. 18 illustrates another embodiment of a drainage system 1400. As illustrated, the drainage system 1400 includes a reservoir 1410 and a vacuum generating member 1430. The reservoir 1410 may be configured as a flexible bag 1411 including an inlet port 1413. A drainage tube 1402 may be coupled to the inlet port 1413 and in fluid communication with the reservoir 1410.

The vacuum generating member 1430 includes an outer housing 1457 defining an outer chamber 1471, an inner housing 1458 defining an inner chamber 1472, a siphon tube 1461, a fluid port 1459, and a drainage port 1460. The outer housing 1457 may be generally cylindrical in shape having a top and a bottom. In other embodiments, the shape of the outer housing 1457 may be elliptical, oval, square, rectangular, etc. The outer housing 1457 may be formed from a rigid or semi-rigid thermoplastic material. For example, the outer housing 1457 may be formed from polycarbonate, polyethylene, polypropylene, polyvinylchloride, etc. The fluid port 1459 is coupled to the top of the outer housing 1457 and is in fluid communication with the outer chamber 1471. The fluid port 1459 is coupled to a distal portion of the drainage tube 1402 that includes a tubing clamp 1401.

The inner housing 1458 is disposed within the outer chamber 1471. The inner housing 1458 may be generally cylindrical in shape having a top and a bottom. In other embodiments, the shape of the inner housing 1458 may be elliptical, oval, square, rectangular, etc. The inner housing 1458 may be formed from the same material as the outer housing 1457. The inner housing 1458 may include a height that is less than the height of the outer housing 1457 and the outer chamber 1471. The inner housing 1458, as illustrated, includes at least one fluid channel 1462 disposed at a lower portion of the inner housing 1458. The fluid channel 1462 is configured to allow fluid to flow from the outer chamber 1471 into the inner chamber 1472.

As depicted, the siphon tube 1461 is disposed within the inner chamber 1472 and includes a height that is less than the height of the inner housing 1458. The siphon tube 1461 may be formed from the same material as the outer and inner housings 1457, 1458. The drainage port 1460 is coupled to the bottom of the outer housing 1457 and is in fluid communication with the siphon tube 1461. The drainage port 1460 is coupled to the drainage tube 1402.

In use, the inlet port 1413 may be coupled to a proximal portion of the drainage tube 1402. The vacuum generating member 1430 may be coupled to the proximal portion and the distal portion of the drainage tube 1402 such that it is disposed between the reservoir 1410 and the tubing clamp 1401. The tubing clamp 1401 may be in a closed state. The drainage system 1400 may be positioned at a level lower than the body cavity intended to be drained. The tubing clamp 1401 may be opened to allow drainage fluid to flow through the drainage tube 1402 from the patient and into the outer chamber 1471 of the vacuum generating member 1430. The outer chamber 1471 may fill with drainage fluid and the drainage fluid may flow through the fluid channel 1462 into the inner chamber 1472. The drainage fluid may fill the inner chamber 1472 until the height of the siphon tube 1461 is achieved and the drainage fluid flows into the siphon tube 1461. The drainage fluid may flow through the drainage port 1460 and the proximal portion of the drainage tube 1402 into the reservoir 1410. When the drainage fluid flows into the siphon tube 1461 from the inner chamber 1472, a vacuum pressure may be generated within the vacuum generating member 1430.

Figure 19B:
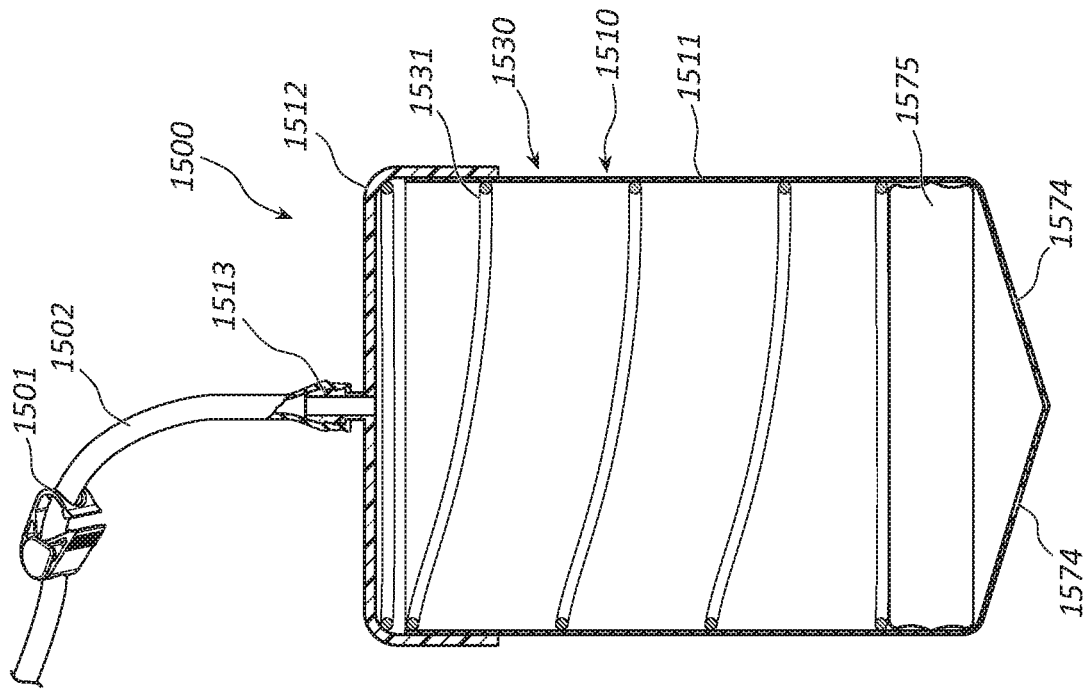
FIG. 19B is a cross-sectional view of the vacuum assisted drainage system of FIG. 19A in an expanded state.
Figure 19A:
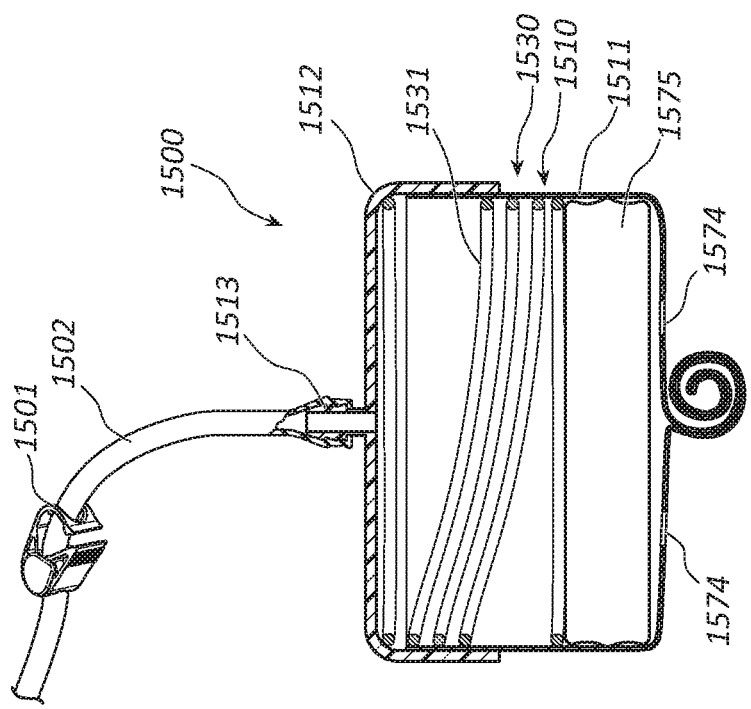
FIG. 19A is a cross-sectional view of a vacuum assisted drainage system with a piston in a collapsed state.

FIGS. 19A-19B depict another embodiment of a drainage system 1500. As depicted, the drainage system 1500 includes a reservoir 1510 and a vacuum generating member 1530. The reservoir 1510 includes a compliant walled housing 1511 and a distal end cap 1512. The distal end cap 1512 includes an inlet port 1513 in fluid communication with the reservoir 1510. A drainage tube 1502 is coupled to the inlet port 1513 and includes a tubing clamp 1501. As illustrated in FIG. 19A, a distal portion of the housing 1511 is coupled to the distal end cap 1512 and a proximal portion is rolled or folded toward the distal portion to provide a compact configuration of the drainage system 1500 when in a collapsed state. FIG. 19B illustrates the drainage system 1500 in an expanded state where the housing 1511 is longitudinally elongated. A proximal end of the housing 1511 is closed and can optionally include a vent channel 1574 configured to vent gas and/or air from a proximal portion of the reservoir 1510. In other embodiments, no vent or vent channels 1574 are used. The rolled or folded portion of the housing 1511 may be configured to unroll or unfold when the vacuum generating member 1530 is activated.

The vacuum generating member 1530 includes a compression spring 1531 and a piston 1575. The compression spring 1531 may be substantially cylindrical in shape where its coils are in longitudinal alignment and are configured to stack upon one another in a compressed state. In another embodiment, the compression spring 1531 may be cone shaped where its coils have a progressively smaller diameter from a proximal portion to a distal portion, such that the coils may be configured to stack within an adjacent coil in the compressed state. As shown, the compression spring 1531 is disposed within the reservoir 1510 between the distal end cap 1512 and the piston 1575. In other embodiments, the compression spring 1531 can be external to the reservoir 1510.

The piston 1575 is disposed within the reservoir 1510 proximal to the compression spring 1531. The piston 1575 may be generally disc shaped and be formed from an elastomeric material. For example, the piston 1575 may comprise silicone, silicone rubber, neoprene, isoprene, thermoplastic elastomer, etc. An outer diameter of the piston 1575 may be larger than an inner diameter of the housing 1511 such that the piston 1575 is sealingly coupled to the housing 1511. The piston 1575 is configured to move from a distal position adjacent the distal end cap 1512 to a proximal position under a force applied by the compression spring 1531. When the piston 1575 moves from the proximal position to the distal position, a vacuum pressure is generated within the reservoir 1510 to assist with drainage of fluid from the patient's body into the reservoir 1510. The vacuum generating member 1530 may be configured to prevent the housing 1511 from collapsing radially inward and/or longitudinally when there is the vacuum pressure inside the housing 1511 by providing a longitudinal tautness to the housing 1511 when the compression spring 1531 applies a proximally directed force to the piston 1575.

In use, the drainage system 1500 is provided to a clinician in the collapsed state to decrease shipping volume. The system 1500 may also optionally be packaged or configured to comprise a vacuum when in the collapsed state. For instance, the reservoir 1510 can be placed in the collapsed state and air and/or fluid can be evacuated from the reservoir 1510. When ready to use, the inlet port 1513 is coupled to the drainage tube 1502, which can comprise a tubing clamp 1501 in a closed state as depicted in FIG. 19A. The tubing clamp 1501 may be opened to activate the vacuum generating member 1530. The compression spring 1531 may apply the proximally directed force to the piston 1575 to move the piston 1575 proximally. As the piston 1575 moves proximally, the vacuum pressure may be generated in the distal portion of the reservoir 1510 and in the drainage tube 1502. The vacuum pressure may initiate flow of drainage fluid from the patient to the reservoir 1510. In some embodiments, the piston 1575 is in intimal contact with the housing 1511 such that when the system is activated, the proximal movement of the piston 1575 forms a pressure differential between the proximal surface of the piston 1575 and the housing 1511, and the distal surface of the piston 1575 and the housing 1511 (e.g., higher pressure (or lesser vacuum) between the proximal surface of the piston 1575 and the housing 1511). This pressure differential can cause a more uniform vacuum in the distal portion of the reservoir 1510, reducing an initial higher vacuum surge in the distal portion of the reservoir 1510 which can cause discomfort and/or pain to the patient.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "about." For each such reference, it is to be understood that, in some embodiments, the value, feature, or characteristic may be specified without approximation. For example, where the "about" is used, this term includes within its scope the qualified word in the absence of their qualifier. For example, where the term "about 120 degrees" is recited with respect to a feature, it is understood that in further embodiments, the feature can have a precisely 120 degrees configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A vacuum assisted drainage system comprising:
   a collapsible reservoir comprising a compliant walled housing;
   a proximal end cap coupled to the compliant walled housing and comprising a proximal coupling member;
   a distal end cap coupled to the compliant walled housing and comprising a distal coupling member configured to engage with the proximal coupling member when the collapsible reservoir is in a collapsed state, wherein the proximal coupling member and the distal coupling member are threaded and configured to occupy a dead space within the collapsible reservoir; and
   a vacuum generating member configured to generate a vacuum pressure within the collapsible reservoir when the collapsible reservoir is changed from the collapsed state to an expanded state having the proximal coupling member disengaged and decoupled from the distal coupling member such that the proximal coupling member and the distal coupling member are spaced from one another,
   wherein the collapsible reservoir comprises a vent valve comprising a flap valve configured to vent gas or air from the collapsible reservoir and a ball valve configured to prevent fluid from exiting the collapsible reservoir.

2. The drainage system of claim 1, wherein the compliant walled housing comprises a concertinaed wall.

3. The drainage system of claim 1, wherein the proximal coupling member of the proximal end cap comprises an externally threaded protrusion and the distal coupling member of the distal end cap comprises an internally threaded receiver configured to receive the externally threaded protrusion when the collapsible reservoir in a collapsed state, wherein the externally threaded protrusion is decoupled and spaced from the internally threaded receiver when the collapsible reservoir is in the expanded state.

4. The drainage system of claim 1, wherein the vacuum generating member comprises a compression spring disposed within or external to the collapsible reservoir.

5. The drainage system of claim 4, wherein the compression spring comprises a plurality of coils in longitudinal alignment.

6. The drainage system of claim 4, wherein the compression spring comprises a plurality of coils configured as a cone, wherein a distal coil of the plurality of coils has a smaller diameter than an adjacent proximal coil of the plurality of coils, and wherein the distal coil is configured to be disposed within the proximal coil when the compression spring is in a compressed state.

7. The drainage system of claim 1, wherein the vacuum generating member comprises a support rod configured to support the collapsible reservoir in an expanded state, and wherein the support rod comprises a plurality of coaxially aligned segments configured to telescope longitudinally relative to one another and to lock in a telescoped state.

8. The drainage system of claim 1, wherein the vacuum generating member comprises a weight removably coupled to the collapsible reservoir.

9. The drainage system of claim 8, wherein the vacuum generating member further comprises a stand configured to suspend the collapsible reservoir, wherein the stand comprises:
 a base;
 a vertically oriented pole coupled to the base;
 a horizontally extending support coupled to the pole; and
 a loading platform moveably coupled to the pole between the horizontally extending support and the base that can be set at different positions to limit the volume of fluid drained.

10. A method of draining fluid from a body cavity, comprising:
 connecting a reservoir to a drainage tube;
 activating a vacuum generating member;
 rotating a reservoir distal cap relative to a reservoir proximal cap to disengage a proximal portion of an internal locking mechanism on the reservoir proximal cap from a distal portion of the internal locking mechanism on the reservoir distal cap, wherein the internal locking mechanism is configured to maintain the reservoir in a collapsed state until the vacuum generating member is activated; and
 expanding the reservoir from a collapsed state to an expanded state having the proximal portion of the internal locking mechanism decoupled and spaced from the distal portion of the locking mechanism to generate a vacuum pressure within the reservoir.

11. The method of claim 10, wherein expanding the reservoir from the collapsed state to the expanded state comprises expanding a compression spring from the compressed state to the expanded state.

12. The method of claim 10, wherein expanding the reservoir from the collapsed state to the expanded state comprises manually displacing a reservoir proximal cap away from a reservoir distal cap and placing a support between the reservoir ends to maintain the reservoir in the expanded state.

13. The method of claim 10, wherein expanding the reservoir from the collapsed state to the expanded state comprises suspending the reservoir from a support and coupling a weight to the reservoir.

14. A vacuum assisted drainage system comprising: a collapsible reservoir comprising:
 a compliant wall;
 a proximal end cap coupled to the compliant wall;
 a distal end cap coupled to the compliant wall; and
 a locking mechanism, wherein the proximal end cap comprises a gap and the distal end cap comprises a radially inward directed lug configured to be received by the gap when the collapsible reservoir is in a collapsed state, wherein the gap and the radially inward directed lug are configured to occupy a space within the collapsible reservoir, and wherein the locking mechanism is disengaged by rotating the distal end cap relative to the proximal end cap; and
 a vacuum generating member configured to generate a vacuum pressure within the collapsible reservoir when the collapsible reservoir is changed from the collapsed state to an expanded state having the radially inward directed lug and the gap spaced from one another,
 wherein the vacuum generating member comprises a compression spring disposed within or external to the collapsible reservoir.

15. The drainage system of claim 14, wherein the distal end cap comprises a vent valve configured to vent gas or air from the collapsible reservoir and to prevent fluid from exiting the collapsible reservoir.

16. The drainage system of claim 1, wherein:
 the distal coupling member includes a plurality of a radially inward directed lugs and the proximal coupling member include a plurality of gaps;
 wherein when the drainage system is in the collapsed state, the plurality of lugs are disposed between and proximal to the plurality of gaps to engage the proximal coupling member with the distal coupling member; and
 wherein when the drainage system is transitioned to the expanded state, the plurality of lugs pass through the plurality of gaps to disengage and decouple the proximal coupling member from the distal coupling member such that the proximal coupling member and the distal coupling member are spaced from one another.

17. The method of claim 10, wherein rotating a reservoir distal cap relative to a reservoir proximal cap to disengage a proximal portion of an internal locking mechanism from a distal portion of the internal locking mechanism includes rotating the reservoir distal cap relative to the reservoir proximal cap to disengage a plurality of radially inward directed lugs of the distal portion of the internal locking mechanism from proximal portion of the internal locking mechanism and pass the plurality of lugs through a plurality of gaps in the proximal portion of the internal locking mechanism.

18. The method of claim 10, wherein rotating a reservoir distal cap relative to a reservoir proximal cap to disengage a proximal portion of an internal locking mechanism from a distal portion of the internal locking mechanism includes rotating the reservoir distal cap relative to the reservoir proximal cap to disengage an externally threaded protrusion of the internal locking mechanism from an internally threaded receiver of the internal locking mechanism.

\* \* \* \* \*